United States Patent
Cook et al.

(10) Patent No.: US 7,635,598 B2
(45) Date of Patent: Dec. 22, 2009

(54) INDUCIBLE FLUORESCENCE ASSAY

(75) Inventors: Ronald M. Cook, Novato, CA (US); Eliana Saxon Armstrong, Richmond, CA (US); Hans E. Johansson, El Cerrito, CA (US)

(73) Assignee: Biosearch Technologies, Inc., Novato, CA (US)

( * ) Notice: Subject to any disclaimer, the term of this patent is extended or adjusted under 35 U.S.C. 154(b) by 0 days.

(21) Appl. No.: 11/177,998

(22) Filed: Jul. 8, 2005

(65) Prior Publication Data

US 2006/0194218 A1    Aug. 31, 2006

Related U.S. Application Data

(60) Provisional application No. 60/586,157, filed on Jul. 8, 2004.

(51) Int. Cl.
*G01N 33/533* (2006.01)
*G01N 33/53* (2006.01)
*C12Q 1/26* (2006.01)
*C12N 1/21* (2006.01)
*C12P 21/00* (2006.01)

(52) U.S. Cl. ............... 436/544; 436/903; 436/56; 435/7.72; 435/25; 435/70.1; 435/252.3

(58) Field of Classification Search ............ 435/7.1, 435/7.9, 7.91, 7.72, 25, 69.1, 69.7, 252.3; 436/544, 546, 904
See application file for complete search history.

(56) References Cited

U.S. PATENT DOCUMENTS 3,523,936 A    8/1970    Toji (Continued)

FOREIGN PATENT DOCUMENTS

EP    0 008 029 A    2/1980

(Continued)

OTHER PUBLICATIONS

Fouts et al. Enzymatic reduction of prontosil and other azo dyes. Journal of Pharmacology and experimental Therapeutics. 1957, vol. 120, Issue 3, pp. 291-300.*

(Continued)

*Primary Examiner*—Shafiqul Haq
(74) *Attorney, Agent, or Firm*—Morgan, Lewis & Bockius, LLP

(57) ABSTRACT

In one aspect, the invention provides fluorescent probes and assays. The probes include a fluorophore-quencher pair that undergoes a switch from dark to fluorescent in response to a reaction of the quencher. The switch of the probe from dark to fluorescent is typically mediated by an enzyme that acts directly or indirectly on the quencher, interfering with its ability to quench fluorescence emission from the fluorophore.

In another aspect, the invention provides a reporter gene assay system and methods of using this system. The assay system includes a fluorophore-quencher probe and an enzyme that acts directly or indirectly on the quencher, increasing the fluorescent emission of the fluorophore. In still other aspects, the invention provides nucleic acid constructs and cells expressing the peptide products of these constructs.

In assays of the invention, the presence of a target substance is detected by the switching of fluorescence mediated by the change in oxidation state of the quencher. The assay systems are of use in numerous assay formats, e.g., confirming the expression of the enzyme that acts on the quencher, and/or detecting a species conjugated to the enzyme.

14 Claims, 14 Drawing Sheets

U.S. PATENT DOCUMENTS

| | | | |
|---|---|---|---|
| 3,996,345 | A | 12/1976 | Ullman et al. |
| 4,482,490 | A | 11/1984 | Imahori et al. |
| 4,687,728 | A | 8/1987 | Folkard et al. |
| 5,312,738 | A | 5/1994 | Hamill et al. |
| 5,401,847 | A | 3/1995 | Glazer et al. |
| 5,612,221 | A | 3/1997 | Simons et al. |
| 5,679,521 | A | 10/1997 | Andersson et al. |
| 5,795,729 | A * | 8/1998 | Lee ............................ 435/24 |
| 6,037,130 | A | 3/2000 | Tyagi |
| 6,117,986 | A | 9/2000 | Nardone et al. |
| 6,124,267 | A | 9/2000 | McEver et al. |
| 6,699,975 | B2 * | 3/2004 | Reed et al. .................. 534/558 |
| 6,790,945 | B2 | 9/2004 | Lukhtanov et al. |
| 6,818,420 | B2 * | 11/2004 | Chou et al. ................. 435/91.2 |
| 7,019,129 | B1 | 3/2006 | Cook et al. |
| 2003/0175728 | A1 * | 9/2003 | Belousov et al. ............... 435/6 |

FOREIGN PATENT DOCUMENTS

| | | |
|---|---|---|
| EP | 0 009 191 A | 4/1980 |
| EP | 0 601 889 A2 | 6/1994 |
| EP | 0 909 823 A2 | 4/1999 |
| FR | 1544951 | 11/1968 |
| JP | 5-142600 | 6/1993 |
| JP | 6-258676 | 9/1994 |
| WO | WO 90/03446 A1 | 4/1990 |
| WO | WO 9502848 A1 | 1/1995 |
| WO | WO 98/10096 A1 | 3/1998 |
| WO | WO 99/64431 | 12/1999 |
| WO | WO 00 05411 A | 2/2000 |
| WO | WO 01/42505 A | 6/2001 |
| WO | WO 03/019145 A | 3/2003 |

OTHER PUBLICATIONS

Susuki et al. Molecular cloning and characterization of the gene coding for azoreductase from *bacillus* sp. OY1-2 isolated from soil. JBC 2001, vol. 276, Issue. 12, pp. 9059-9065.*

Rafii et al. Cloning and expression in *Escherichia coli* of an azoreductase gene from *Clostridium* perfringes and comparison with azoreductase genes from other bacteria. J. Basic Microbiol. 1999, vol. 39, No. 1, pp. 29-35.*

Fouts, et al., "Enzymatic Reduction of Prontosil and Other Azo Dyes," *Journal of Pharmacology and Experimental Therapeutics*, vol. 120, Issue 3, pp. 291-300 (1957).

Murakami, et al., "Characterization of Intermolecular Electron Transfer Pathway From 2-Hydroxyphenazine to Hterodisulfide Reductase From Methanosarcina Thermophila," *J. Biol. Chem.*, 276(4):2432-2439 (2001).

Suzuki, et al., "Molecular Cloning and Characterization of the Gene Coding for Azoreductase From *bacillus* sp. OY1-2 Isolated From Soil," *J. Biol. Chem.*, 276(12):9059-9065 (2001).

Wataru Sugiura, et al., "Expression and Characterization of the Genes Encoding Azoreductases from *Bacillus subtilis* and *Geobacillus stearothermophilus*," *Biosci. Biotechnol. Biochem*, 70(7):1655-1665 (2006).

Huizhong Chen, "Recent Advances in Azo Dye Degrading Enzyme Research," *Current Protein and Peptide Science*, 7:101-111 (2006).

Ito, et al., "Three-dimensional Structure of AzoR from *Escherichia coli*," The *Jourmal of Biological Chemistry*, 281(29):20567-20576 (Jul. 21, 2006).

Deller, et al., "Characterization of a Thermostable NADPH:FMN Oxidoreductase From the Mesophilic Bacterium *Bacillus subtilis*," *Biochemistry*, 45:7083-7091 (2006).

Hodgkiss et al., "Biochemical Pharmacology", vol. 41, No. 4, pp. 533-541, 1991.

Ediss et al., International Journal of Applied Radiation and Isotopes 1982, 33(4) pp. 296-297.

Uzdensky, "Isolated Nerve Cell Response to Laser Irradiation and Photodynamic Effect", De la Cellule au Cerveau, From Cell to Brain: Intra- and Inter-Cellular Communication, The Central Nervous System, Les Houches, Session LXV, 1996.

Endo et al. (Chemical Abstract vol. 64, 1228e, 1966).

Tyagi, et al., "Molecular beacons: Probes that fluoresce upon hybridization," Nature Biotechnology, 14:303-308 (Mar. 1996).

Bumelis, et al., Database CA 'Online!, Chemical Abstracts Service, Columbus Ohio, U.S.; Database accession No. 85:125772 XP002243719 (Abstract only) (1974).

Gonzalez-Gomez, et al., Database CA 'Online!, Chemical Abstracts Service, Columbus Ohio, U.S.; Database accession No. 98:209380 XP002243718.

Jerzy et al., Database CA 'Online!, Chemical Abstracts Service, Columbus Ohio, U.S.; Database accession No. 110:136859 XP002243716 (Abstract only) (1988).

Juarranz, et al., Database CA 'Online!, Chemical Abstract Service, Columbus Ohio, U.S.; Database accession No. 105:338550 XP002243717 (Abstract only) (1986).

Kazimierz, Database CA 'Online!, Chemical Abstracts Service, Columbus Ohio, U.S.; Database accession No. 131:287725 XP002243715 (Abstract only) (1995).

Riccardo, et al., Database CA 'Online!, Chemical Abstract Service, Columbus Ohio, U.S.; Database accession No. 122:215261 XP002273714 (Abstract only) (1995).

Chou, et al., "Use of Dark-Quenched Fret Probes Real Time PCT," *American Biotechnology Laboratory*, 19(8):34; XP009012130 (Aug. 2001).

Juarranz, et al., "Prediction of in situ Fluorescence of Histochemical Reagents Using a Structure-Staining Correlation Procedure," *Histochemistry*, 84(4-6):426-431 (Jun. 1986).

Marras, et al., "Efficiences of Fluorescence Resonance Energy Transfer and Contact-Mediated Quenching in Oligonucleotide Probes," *Nucleic Acids. Res.*, 30(21):1-8 (2002).

Marshall, et al., "The Composition of Stains Produced by the Oxidation of Methylene Blue," *Histochemical Journal*, 8:431-442 (1976).

Marshall, et al., "A Technique for Distinguishing Between Methylene Violet and Methylene Violet Bernthsen," *Stain Technology*, 50(1):51-53 (Jan. 1975).

Medina, et al., "Thin-Layer Chromatographic Detection of Zeranol and Estradiol in Fortified Plasma and Tissue Extracts with Fast Corinth V," *J. Chrom. Biomedical Applications*, 581(1):119-128 (Oct. 2, 1992).

Medina, et al., "Improved Thin-Layer Chromatographic Detection of Diethylstilbestrol and Zeranol in Plasma and Tissues Isolated with Alumina and Ion-Exchange Membrane Columns in Tandem," *J. Chrom.*, 614:315-323 (Jan. 21, 1993).

Moreira, et al., "Effects of Fluorescent Dyes, Quenchers, and Dangling Ends of DNA Duplex Stability," *Biochem Biophys. Res. Commun.*, 327:473-484 (Feb. 25, 2005) published on-line Dec. 15, 2004.

Pelander, et al., "Preparation of N-Demethylated Drug Metabolites for Analytical Purposes Using 1-Chloroethyl Chloroformate," *Forensic Science International*, 85:193-198 (1997).

Pelander, et al., "Screening for Cyanobacterial Toxins in Bloom and Strain Samples by Thin Layer Chromatography," *Water Research*, 30(6):1464-1470 (1996).

Sahlin, et al., "Differentiation Between Attached and Ingested Immune Complexes by a Fluorescence Quenching Cytofluorometric Assay," *J. Immun. Methods*, 60:115-124 (1983).

Xie, et al., "Synthesis and Non-Linear Optical Properties of Four Polyurethanese Containing Different Chromophore Groups," *European Polymer Journal*, 37:497-505 (2001) and *Chemical Abstracts Service*, XP002243721; STN Database Accession No. 134:296174.

* cited by examiner

1: pellet solubilized in 8M urea
2: flow through
3: denaturing wash
4: refolding wash
5: elution fraction 1
6: elution fraction 2
7: elution fraction 3
8: elution fraction 4
9: elution fraction 5

Buffer 1: Dubelcco's PBS (no enzyme)
Buffer 2: Dubelcco's PBS
Buffer 3: Dubelcco's PBS + Mg + Ca
Buffer 4: PBS
Buffer 5: Tris
Buffer 6: Tris + Mg
Buffer 7: Tris + Ca
Buffer 8: Tris + Mg + Cl

FIGURE 9

ATGAAACTAGTCGTTATTAACGGTACACCAAGAAAATTTGGTAGAACTCGCGTGGTGGCAA
AATATATTGCGGATCAATTTGAAGGGGAATTATATGATTTAGCAATTGAGGAGTTACCTTTAT
ACAATGGAGAAGAGTCGCAACGTGATTTAGAGGCAGTAAAAAAATTAAAAACGTTAGTGAAA
GCTGCGGATGGGGTTGTATTATGTACACCAGAATATCATAATGCGATGAGCGGTGCGCTGAAA
AACTCTTTAGATTACTTAAGTAGTAGTGAATTTATTCATAAACCAGTTGCATTGTTAGCGGTTG
CTGGTGGCGGTAAAGGTGGAATAAATGCATTAAACAGCATGCACGCGTCGCTAGCAGGTGTT
TATGCAAATGCAATTCCAAAACAAGTTGTGCTTGATGGATTACATGTGCAAGATGGTGAACTT
GGGGAAGATGCAAAACCATTAATTCATGATGTAGTTAAAGAATTGAAAGCATATATGAGCGT
ATATAAGAGGTGAAAAAACAACTAGGAGTGGAGTGA

SEQ ID NO. 3

FIGURE 10

| | |
|---|---|
| SEQ ID NO. 1 | ATG AAA CTA GTC GTT ATT AAC GGT ACA CCA AGA AAA TTA GGT AGA |
| SEQ ID NO. 2 | M   K   L   V   V   I   N   G   T   P   R   K   L   G   R |

```
SEQ ID NO. 1    ATG AAA CTA GTC GTT ATT AAC GGT ACA CCA AGA AAA TTA GGT AGA
SEQ ID NO. 2     M   K   L   V   V   I   N   G   T   P   R   K   L   G   R

ACT CGC GTT GTG GCA AAA TAT ATT GCA GAT CAA TTT GAA GGG GAA
                 T   R   V   V   A   K   Y   I   A   D   Q   F   E   G   E

TTA TAC GAT TTA GCA ATA GAG GAA TTG CCT TTA TAT AAT GGC GAA
                 L   Y   D   L   A   I   E   E   L   P   L   Y   N   G   E

GAA TCG CAA CGT GAT TTA GAG GCA GTA AAA AAA TTA AAA GCG TTA
                 E   S   Q   R   D   L   E   A   V   K   K   L   K   A   L

GTG AAA GCA GCA GAC GGT GTA GTA CTA TGT ACA CCA GAA TAT CAT
                 V   K   A   A   D   G   V   V   L   C   T   P   E   Y   H

AAT GCA ATG AGC GGA GCG CTG AAA AAC TCG TTA GAT TAC TTA AGT
                 N   A   M   S   G   A   L   K   N   S   L   D   Y   L   S

AGT AGT GAG TTT ATC CAT AAA CCT GTC GCA TTA CTA GCT GTT GCG
                 S   S   E   F   I   H   K   P   V   A   L   L   A   V   A

GTT GCT AGA GGT GTT TAC GCA AAT GCA ATC CCA AAA CAA GTA GTA
                 V   A   R   G   V   Y   A   N   A   I   P   K   Q   V   V

GGG GGC GGT AAA GGA GGA ATT AAC GCA TTA AAT AGT ATG CGA ACT
                 G   G   G   K   G   G   I   N   A   L   N   S   M   R   T

CTT GAT GGA CTT CAC GTA CAA GAT GGT GAA CTT GGA GAA GAT GCA
                 L   D   G   L   H   V   Q   D   G   E   L   G   E   D   A

AAA CCA TTA ATT CAT GAT GTA GTT AAA GAA TTA AAA GCA TAT ATG
                 K   P   L   I   H   D   V   V   K   E   L   K   A   Y   M

AGC GTA TAT AAA GAG GTG AAA AAA CAA CTA GGA GTG GAG TGA
                 S   V   Y   K   E   V   K   K   Q   L   G   V   E   Stop
```

FIGURE 11

FIGURE 14
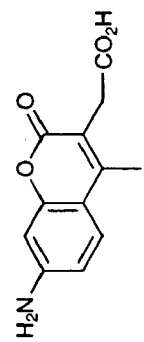
AMCA
$\lambda_{max}$ abs 350
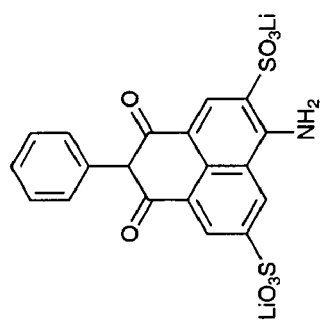
Lucifer yellow
$\lambda_{max}$ abs 428 nm
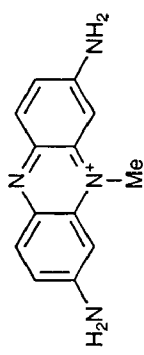
Acriflavin
$\lambda_{max}$ abs 462 nm
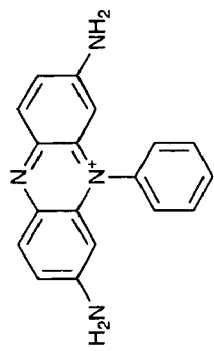
Safranin O
$\lambda_{max}$ abs 530 nm

INDUCIBLE FLUORESCENCE ASSAY

BACKGROUND OF THE INVENTION

1. Field of Invention

The present invention relates generally to fluorescent probes and assays. The probes include a quencher having a moiety that, upon undergoing a change in oxidation state, ceases to act as a quencher of fluorescence. In assays of the invention, the presence of a target substance is detected by the switching of fluorescence mediated by the change in oxidation state of the quencher.

2. Background

There is a continuously expanding need for rapid, highly specific methods of detecting and quantifying chemical, biochemical and biological substances as analytes in research and diagnostic mixtures. Of particular value are methods for measuring small quantities of nucleic acids, peptides, saccharides, pharmaceuticals, metabolites, microorganisms and other materials of diagnostic value. Examples of such materials include narcotics and poisons, drugs administered for therapeutic purposes, hormones, pathogenic microorganisms and viruses, peptides, e.g., antibodies and enzymes, and nucleic acids, particularly those implicated in disease states.

The presence of a particular analyte can often be determined by binding methods that exploit the high degree of specificity that characterizes many biochemical and biological systems. Frequently used methods are based on, for example, antigen-antibody systems, nucleic acid hybridization techniques and protein-ligand systems. In these methods, the existence of a complex of diagnostic value is typically indicated by the presence or absence of an observable "label" which is attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

In addition to, or rather than, being directly detected, many dye labels operate to quench the fluorescence of an adjacent second fluorescent label. Because of its dependence on the distance and the magnitude of the interaction between the quencher and the fluorophore, the quenching of a fluorescent species provides a sensitive probe of molecular conformation and binding, as well as other interactions. An exemplary application of fluorescent reporter quencher pairs is found in the detection and analysis of nucleic acids.

Fluorescent nucleic acid probes are important tools for genetic analysis, in both genomic research and development, and in clinical medicine. As information from genome projects accumulate, the level of genetic interrogation mediated by fluorescent probes will expand enormously. One particularly useful class of fluorescent probes includes self-quenching probes, also known as fluorescence energy transfer probes, or FET probes. The design of different probes using this motif may vary in detail. In an exemplary FET probe, both a fluorophore and a quencher are tethered to a nucleic acid. The probe exists in a conformation in which the fluorophore is proximate to the quencher and the probe produces a signal only as a result of its hybridization to an intended target, separating the fluorophore and quencher. Despite the limited availability of FET probes, techniques incorporating their use are rapidly displacing alternative methods.

Fluorescent-based reporter gene assays are also known. The most general reporter systems are those that encode an enzyme that acts upon a small molecule substrate to produce a colorimetric or fluorescent signal. Fluorescence is a significantly more sensitive technique, particularly amongst a background of cellular matter (Naylor, Biochem. Pharmacol., 58: 749-757 (1999)). Pro-fluorescent substrates have been developed for β-lactamase, β-galactosidase, β-glucuronidase, horseradish peroxidase and alkaline phosphatase (Schenborn et al., Mol. Biotechnol., 13: 29-44 (1999)). These enzymes all act upon their substrates to remove an epitope that quenches fluorescence (the first three cleave a glycosidic linkage, horseradish peroxidase oxidizes saturated bonds to conjugated alkenes and alkalinephosphatase hydrolyzes a phosphate ester). These enzymes are commonly applied for both in vitro and in vivo assays. Alkaline phosphatase has been engineered to create a secreted form, eliminating the need to lyse host cells to measure activity (Berger et al., Gene 66: 1-10 (1988)). This is a significant advantage since many cell types possess endogenous phosphatases that can produce high background in the experiment. However, both alkaline phosphatase and horseradish peroxidase are widely used as reporter conjugates in in vitro applications where competing enzymatic activity is excluded.

One of the earliest assay systems designed to monitor cellular transcriptional activity made use of chloramphenicol acetyltransferase (CAT), an enzyme originating from E. coli (Gorman, Mol. Cell. Biol. 2: 1044-1051 (1982)). The assay for the expression of the enzyme involves the substrate $^{14}$C-labeled chloramphenicol, which is acetylated by CAT. The amount of radioactive product is quantified after isolation by thin layer chromatography (TLC). The background activity of CAT is negligible in mammalian cells and the threshold for detection of radioactivity is quite low. However, the need for radioactive isotopes and purification of the acetylated chloramphenicol hinder the use of this system due to cost and hazardous waste production. Recently developed fluorescent CAT substrates (Invitrogen) do not obviate the need for time consuming TLC.

Green fluorescent protein (GFP) is a popular reporter gene (Tsien, Annu. Rev. Biochem. 67: 509-544 (1998)). GFP is not an enzyme, but rather a protein that folds to form an intrinsic fluorophore. This is especially useful for protein localization experiments. Since no substrate is needed there is no risk of perturbing the cell by the addition of a potentially toxic small molecule. Another common problem with exogenous substrates is that many are not membrane permeable and so the cell must be ruptured for contact with the enzyme. Efforts to develop new variants of GFP that fluoresce in different colors have been successful, yielding both cyan and yellow fluorescent proteins (Sawano et al., Nucl. Acids Res., 28: E78 (2000)). Current drawbacks to the use of GFP are the length of time required for fluorophore formation and low sensitivity without the signal amplification that arises from enzymatic turnover.

Inducible fluorescent signals are essential components of genomic, biochemical, and immunoassays. Modern drug discovery platforms require rapid identification of interactions between targets and small molecules. Often such assays rely upon enzymatic activity that generates a fluorescent signal.

While many fluorescence-based assays are applied in vitro, reporter genes are designed to be observable within a cell or whole organism thus providing key information about protein-protein interactions and gene expression in vivo. Identifying enzyme/substrate pairs with sufficient specificity and sensitivity for these applications is a significant challenge. The present invention provides a strategy to match an enzyme with a panel of pro-fluorescent substrates, thereby creating a system that is readily adaptable to a wide range of environments and diverse fluorescence signals.

BRIEF SUMMARY OF THE INVENTION

As scientists continue to probe the intricacies of life at the molecular level, the need for reporters capable of translating a microscopic event into an observable signal grows (Zhang et al., *Nat. Rev. Mol. Cell. Biol.* 3: 906-918 (2002)). For such applications it is recognized that "switching on" a fluorescent signal is preferable to "switching off" a calorimetric one. This is due to the greater sensitivity and superior spatial and temporal resolution of fluorescence assays (de Silva et al., *Chem. Rev.* 97: 1515-1566 (1997); and D'Auria et al., *Curr. Opin. Biotechnol.* 12: 99-104 (2001)). The detectable fluorescent signal generally arises either from the generation of a fluorophore or separating a fluorophore from operative proximity with a quencher to reveal extant fluorescence.

Accordingly, the present invention provides intramolecularly quenched probes that include a quencher moiety that is an enzyme substrate or susceptible to reaction with the product of an enzyme reaction. The invention also provides novel assays using the probes of the invention.

Exemplary methods of the present invention are based on the reaction of a probe quencher moiety with an enzyme or a reaction product of an enzyme. The quencher is converted to a species that quenches fluorescence from the fluorophore less efficiently than the original quencher, generating an increase in fluorescence.

Alternatively, the methods utilize the cleavage of a bond internal to a non-fluorescent or minimally fluorescent species. The bond cleavage causes one of the moieties previously linked by the cleaved bond to become fluorescent. In essence, this embodiment involves the dissociation of a "pro-fluorophore" from a moiety that quenches the fluorescence from the "pro-fluorophore." As discussed above, the cleavage is preferably mediated by an enzyme or a reaction product of an enzyme.

Enzyme mediated chemical transformations are critical steps in a variety of synthetic and analytical procedures, at both the investigative and industrial scale. The widespread utility of enzymes as catalysts is partly a result of their unparalleled substrate specificity. In addition, the ability to operate under mild conditions avoids interference with coexisting processes or functional groups. Moreover, ongoing efforts to identify highly stable enzymes from extremophiles (Schiraldi et al., *Trends Biotechnol.* 12: 515-521 (2002); and Hough *Curr. Opin. Chem. Biol.* 3: 39-46 (1999) or to engineer tolerance of non-native conditions have met with success (Giver et al., *Proc. Natl. Acad. Sci. USA* 95: 12809-12813 (1998); Sterner et al., *Crit. Rev. Biochem. Mol. Biol.* 36: 39-106 (2001)).

Reductases, e.g. azoreductases, and quinone reductases are poised for biotechnological applications because their activity is both well studied and readily monitored. Substrate specificity studies have examined representative reductase enzymes in an effort to define a clear structure activity relationship (Rafii et al., *J. Basic. Microbiol.*, 39: 29-35 (1999); and Elliott, *Carcinogenesis* 5: 1051-1055 (1984)). Although a few characteristics indicative of a reactive substrate have been identified, such as a preference for electron donating groups on the aromatic rings, there are as many possibilities for geometry and number of substituents on a reductase substrate as there are reductase-producing organisms.

Previous applications of azoreductases, such as wastewater treatment, have focused on decomposition of a target substrate with little interest in the fate of the cleavage products. Another application relies on intestinal azoreductases to provide an active drug from an inactive azo prodrug. Balsalazine and Olsalazine are effective treatments for inflammatory bowel disease that release 5-aminosalicylic acid upon reaching the colon where the resident microflora carry out cleavage of an azo bond masking the amino group. Similarly, polymeric carriers decorated with azo linked drugs result in improved bioavailability. See, Chourasia et al., *J. Pharm. Pharm. Sci.* 6: 33-66 (2003).

In contrast to earlier methods, the present invention provides inducible fluorescence assays and probes of use in these assays. The probes include a fluorophore-quencher pair that undergoes a switch from dark to fluorescent in response to a reaction of the quencher. The switch of the probe from dark to fluorescent is generally mediated by an enzyme that acts directly or indirectly on the quencher, interfering with its ability to quench fluorescence emission from the fluorophore. Interruption of the quencher's ability to quench fluorescence emission from the fluorophore generates a fluorescent signal or an increases an existing signal. When the quencher is a substrate for the enzyme, the enzyme can act directly on the quencher. Alternatively, the enzyme may act indirectly on the quencher, generating a species that reacts with the quencher.

Also provided is a reporter gene assay system and methods of using this system. The assay system includes a fluorophore-quencher probe and an enzyme that acts directly or indirectly on the quencher, increasing the fluorescent emission of the fluorophore. Nucleic acid constructs and cells expressing the peptide products of these constructs are also provided. The assay system is of use in numerous assay formats, e.g., confirming the expression of the enzyme that acts on the quencher, and detecting a species conjugated to the enzyme.

Other aspects, embodiments and objects of the present invention will be apparent from the detailed description that follows.

BRIEF DESCRIPTION OF THE DRAWINGS

FIG. 9 is a nucleic acid sequence for an azoreductase showing the location of the 5'- and 3'-primers used for amplifying the azoreductase DNA sequence. Primer sequences are indicated in bold.

FIG. 10 is a nucleic acid sequence (SEQ ID NO:1) aligned with a peptide sequence (SEQ ID NO:2) for the azoreductase that it encodes.

FIG. 11 Multiple sequence alignment of azoreductase protein sequences from *B. subtilis* (BACSU), *B. cereus* (BACCE) and *S. cerevisiae* (SACCE). Sequences were aligned with CLUSTAL_X and identical residues (black) shaded with a 90% cutoff with BOXSHADE (http://www.ch.embnet.org/software/BOX_form.html). ●: FMN binding site residues: Cys70; Loop I and Loop II: Putative substrate specificity loops.

FIG. 14 Shows some exemplary amino-substituted fluorescent molecules.

DETAILED DESCRIPTION OF THE INVENTION

Abbreviations

Figure 1:
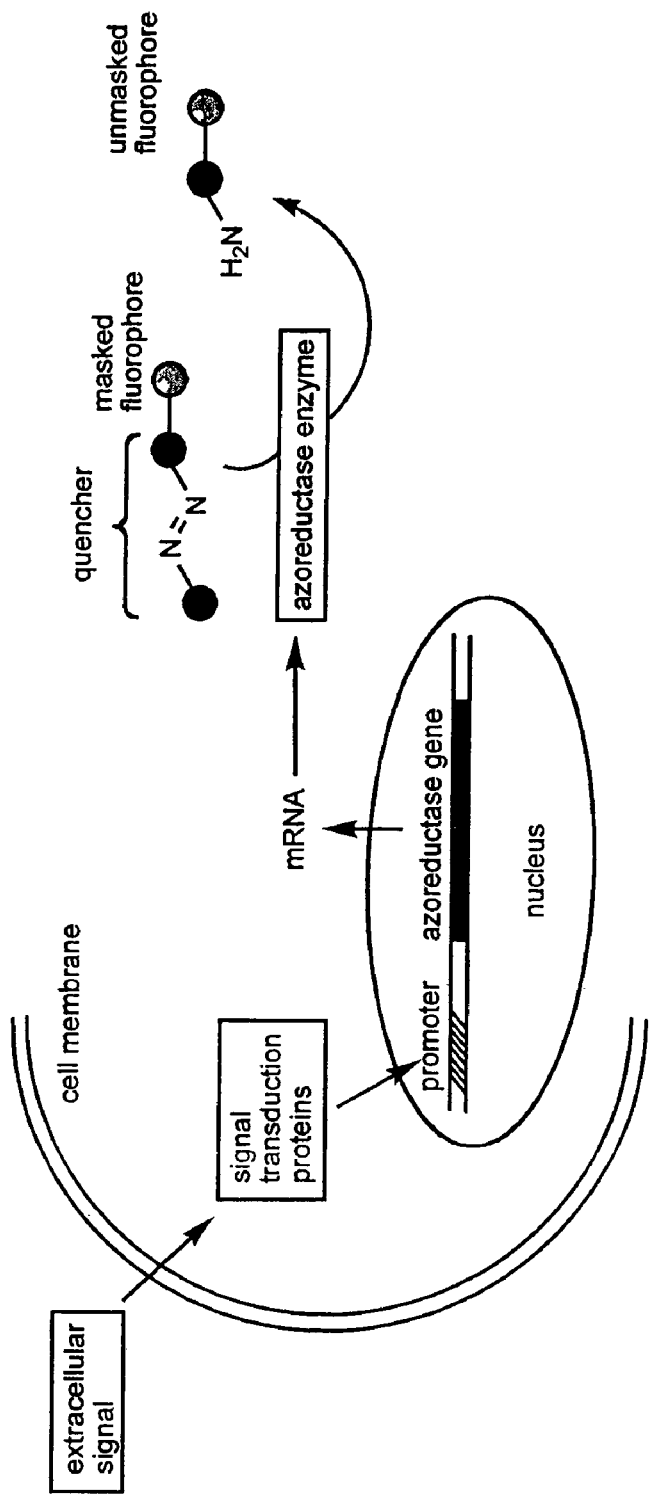
FIG. 1 is an exemplary azoreductase reporter gene assay of the invention. The presence of the appropriate analyte (extracellular signal) triggers expression of the azoreductase enzyme. An appropriate cell permeable substrate will undergo cleavage of the azo bond to produce a fluorescent product.

"FET," as used herein, refers to "Fluorescence Energy Transfer."

"FRET," as used herein, refers to "Fluorescence Resonance Energy Transfer." These terms are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer."

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2000) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications thereof. Unless otherwise indicated, a particular nucleic acid sequence includes the complementary sequence thereof.

Modifications include, but are not limited to, conjugation with a compound of the invention or a construct that includes a compound of the invention covalently attached to a linker that tethers the compound to the nucleic acid, and those providing the nucleic acid with a group that incorporates additional charge, polarizability, hydrogen bonding, electrostatic interaction, fluxionality or functionality to the nucleic acid. Exemplary modifications include the attachment to the nucleic acid, at any position, of one or more hydrophobic or hydrophilic moieties, minor groove binders, intercalating agents, quenchers, chelating agents, metal chelates, solid supports, and other groups that are usefully attached to nucleic acids.

Exemplary modified nucleic acids include, but are not limited to, peptoid nucleic acids (PNAs), those with phosphodiester group modifications (e.g., replacement of O⁻ with OR, NR, or SR), 2'-, 3'- and 5'-position sugar modifications, modifications to the base moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of $P(O)O_3$ with another moiety, methylations, unusual base-pairing combinations such as the isobases, isocytidine and isoguanidine and the like. Nucleic acids can also include non-natural bases, e.g., nitroindole. Non-natural bases include bases that are modified with a compound of the invention or a linker-compound of the invention construct, a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

"Nucleic acid" also includes species that are modified at one or more internucleotide bridge (e.g., $P(O)O_3$) by replacing or derivatizing an oxygen of the bridge atom with a probe of the invention, fluorophore, quencher, intercalator, hybridization enhancer, chelating agent, metal chelate or minor groove binder, or one of these species attached to a linker. For example, "nucleic acid" also refers to species in which the P(O)O$_2$ moiety (the O$^-$ moiety remains unchanged or is converted to "OR") of a natural nucleic acid is replaced with a non-natural linker species, e.g., —ORP(O)O—, —ROP(O)R—, —ORP(O)OR— —ROP(O)OR— or —RP(O)R— in which the symbol "—" indicates the position of attachment of the linker to the 2'-, 3'- or 5'-carbon of a nucleotide sugar moiety, thus allowing the placement of the exemplified, and other, non-natural linkers between adjacent nucleoside sugar moieties. Exemplary linker subunits ("R") include substituted or unsubstituted alkyl and substituted or unsubstituted heteroalkyl moieties. "R" can include a probe of the invention, fluorophore, quencher, intercalator, hybridization enhancer, chelating agent, metal chelate or minor groove binder, or one of these species attached to a linker.

Furthermore, "nucleic acid" includes those species in which one or more internucleotide bridge does not include phosphorus: the bridge being optionally modified with a probe of the invention, fluorophore, quencher, intercalator, hybridization enhancer, chelating agent, metal chelate or minor groove binder, or a linker construct including one of these species. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a fluorophore, quencher, intercalator, hybridization enhancer, chelating agent, metal chelate or minor groove binder, or a linker construct that includes one of these species. The discussion above is not limited to moieties that include a carbon atom as the point of attachment; the locus can also be another appropriate linking atom, such as nitrogen or another atom.

As used herein, "quenching group" refers to any fluorescence-modifying group of the invention that can attenuate at least partly the fluorescence emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group. In an exemplary embodiment, the quencher operates through a ground state complex (static quenching), rather than through FRET, which requires spectral overlap of the fluorophore and quencher.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Bioactive species," refers to molecules that, when administered to an organism, affect that organism. Exemplary bioactive species include pharmaceuticals, pesticides, herbicides, growth regulators and the like. Bioactive species encompasses small molecules (i.e., approximately <1000 daltons), oligomers, polymers and the like. Also included are nucleic acids and their analogues, peptides and their analogues and the like.

"Carrier molecule," as used herein refers to any molecule to which a probe of the invention is attached. Alternatively, a carrier molecule refers to a molecule to which an enzyme, which reacts (directly or indirectly) with a quencher of a probe of the invention, is attached. Representative carrier molecules include a protein (e.g., enzyme, antibody), glycoprotein, peptide, saccharide (e.g., mono- oligo- and polysaccharides), hormone, receptor, antigen, substrate, metabolite, transition state analog, cofactor, inhibitor, drug, dye, nutrient, growth factor, etc., without limitation. An exemplary carrier molecule is, or includes, a "targeting moiety." "Carrier molecule" also refers to species that might not be considered to fall within the classical definition of "a molecule," e.g., solid support (e.g., synthesis support, chromatographic support, membrane), virus and microorganism.

A "targeting moiety" is a molecule or a region of a molecule that recognizes and interacts with a selected target. An exemplary targeting moiety is an antibody. Other exemplary targeting moieties rely on ligand-receptor interactions, and other recognized molecular recognition events. A targeting moiety can be used to target a probe of the invention or an enzyme that interacts with a probe of the invention to a specific component of a sample, region of a sample, cell, tissue, etc.

"Operative proximity," as used herein refers to the positional relationship between the quencher and the fluorophore, e.g., on a probe. When the quencher and fluorophore are in "operative proximity," the quencher quenches at least a portion of the fluorescence emitted by the fluorophore. Exemplary mechanisms by which the emission from the fluorophore is quenched include static quenching, FET and FRET.

Where chemical moieties are specified by their conventional chemical formulae, written from left to right, they equally encompass the moiety which would result from writing the structure from right to left, e.g., —CH$_2$O— is intended to also recite —OCH$_2$—; —NHS(O)$_2$— is also intended to represent. —S(O)$_2$HN—, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene" and those derivatives of alkyl defined in more detail below, such as "heteroalkyl." Alkyl groups, which are limited to hydrocarbon groups, are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multi-valent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) ("alkyl group substituents") can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups ("aryl group substituents") are varied and are selected from, for example: halogen, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

"Analyte," "target," "substance to be assayed", and "target species," as utilized herein refer to the species of interest in an assay mixture. The terms refer to a substance, which is detected qualitatively or quantitatively using a material, process or device of the present invention. Examples of such substances include cells and portions thereof, enzymes, antibodies, antibody fragments and other biomolecules, e.g., antigens, polypeptides, glycoproteins, polysaccharides, complex glycolipids, nucleic acids, effector molecules, receptor molecules, enzymes, inhibitors and the like and drugs, pesticides, herbicides, agents of war and other bioactive agents.

More illustratively, such substances include, but are not limited to, tumor markers such as α-fetoprotein, carcinoembryonic antigen (CEA), CA 125, CA 19-9 and the like; various proteins, glycoproteins and complex glycolipids such as $β_2$-microglobulin ($β_2$ m), ferritin and the like; various hormones such as estradiol (E$_2$), estriol (E$_3$), human chorionic gonadotropin (hCG), luteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the analyte and other components. The other components are, for example, diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

The term "drug" or "pharmaceutical agent," refers to bioactive compounds that cause an effect in a biological organism. Drugs used as affinity moieties or targets can be neutral or in their salt forms. Moreover, the compounds can be used in the present method in a prodrug form. Prodrugs are those compounds that readily undergo chemical changes under physiological conditions to provide the compounds of interest in the present invention.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell.

The term "swapping" refers to the recombinant manipulation of nucleic acid sequence or amino acid sequence to construct the fusion proteins of the invention as described herein, and is not limited to the exchange or replacement of nucleic acid sequences or amino acid sequences. For example, nucleic acid sequence or amino acid sequence can be extended, shortened or modified to construct the fusion proteins of the invention. Also for example, a nucleic acid sequence or amino acid sequence of a first polypeptide can be modified to contain sequences that are substantially identical to the nucleic acid sequence or amino acid sequence, respectively, of a second polypeptide and, thereby, a "fusion protein" is constructed.

A "fusion protein" refers to a protein comprising amino acid sequences that are in addition to, in place of, less than, and/or different from the amino acid sequences encoding the original or native full-length protein or subsequences thereof.

Components of fusion proteins include "accessory enzymes" and/or "purification tags." An "accessory enzyme" as referred to herein, is an enzyme that forms a reactive species that reacts with a quencher of a probe of the invention. An accessory enzyme can, for example, catalyze the formation of a reducing agent that reacts with the quencher. An accessory enzyme can also be one that generates an active species from a masked reactive species (e.g., ascorbic acid ester→ascorbic acid).

The terms "expression level" or "level of expression" with reference to a protein refers to the amount of a protein produced by a cell. In a preferred embodiment, the protein is a recombinant reductase fusion protein having a "high" level of expression, which refers to an optimal amount of protein useful in the methods of the present invention. The amount of protein produced by a cell can be measured by the assays and activity units described herein or known to one skilled in the art. One skilled in the art knows how to measure and describe the amount of protein produced by a cell using a variety of assays and units, respectively. Thus, the quantitation and quantitative description of the level of expression of a protein, e.g., a reductase, is not limited to the assays used to measure the activity or the units used to describe the activity, respectively. The amount of protein produced by a cell can be determined by standard known assays, for example, western blotting, ELISA, the protein assay by Bradford (1976), the bicinchoninic acid protein assay kit from Pierce (Rockford, Ill.), or as described in U.S. Pat. No. 5,641,668.

The term "enzymatic activity" refers to an activity of an enzyme and may be measured by the assays and units described herein or known to one skilled in the art. Examples of an activity of a reductase include, but are not limited to, those associated with the functional domains of the enzyme, e.g., acceptor substrate specificity, catalytic activity, binding affinity, anchoring to a cell membrane, or other biological or biochemical activity. In a preferred embodiment, the enzyme has "high" enzymatic activity which refers to an optimal level of enzymatic activity measured by the assays and units described herein or known to one skilled in the art (see, e.g., U.S. Pat. No. 5,641,668). One skilled in the art would know how to measure and describe an enzyme activity using a variety of assays and units, respectively. Thus, the quantitation and quantitative description of an enzymatic activity of a reductase is not limited to the assays used to measure the activity or the units used to describe the activity, respectively.

The term "specific activity" as used herein refers to the catalytic activity of an enzyme, e.g., a recombinant reductase fusion protein of the present invention, and may be expressed in activity units. As used herein, one activity unit catalyzes the formation of 1 µmol of product per minute at a given temperature (e.g., at 37° C.) and pH value (e.g., at pH 7.5). Thus, 10 units of an enzyme is a catalytic amount of that enzyme where 10 µmol of substrate are converted to 10 µmol of product in one minute at a temperature of, e.g., 37° C. and a pH value of, e.g., 7.5.

A "catalytic domain" refers to a protein domain, or a subsequence thereof, that catalyzes an enzymatic reaction performed by the enzyme. For example, a catalytic domain of a reductase will include a subsequence of the reductase sufficient to transfer an electron from a donor to an acceptor. A catalytic domain can include an entire enzyme, a subsequence thereof, or can include additional amino acid sequences that are not attached to the enzyme, or a subsequence thereof, as found in nature.

A "subsequence" refers to a sequence of nucleic acids or amino acids that comprise a part of a longer sequence of nucleic acids or amino acids (e.g., protein) respectively.

A "recombinant expression cassette" or simply an "expression cassette" is a nucleic acid construct, generated recombinantly or synthetically, with nucleic acid elements that are capable of expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "heterologous sequence" or a "heterologous nucleic acid", as used herein, is one that originates from a source foreign to the particular host cell, or, if from the same source, is modified from its original form. Thus, a heterologous reductase gene in a eukaryotic host cell includes a reductase-encoding gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components that interfere with the activity of an enzyme. In general, the term "isolated" refers to material that is substantially or essentially free from components that normally accompany the material as found in its native state. Typically, an isolated saccharide, protein, or nucleic acid is at least about 80% pure, usually at least about 90%, and preferably at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and HPLC or a similar means for purification, for example, may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or proteins, refers to two or more sequences or subsequences that have at least greater than about 60% nucleic acid or amino acid sequence identity, 65%, 70%, 75%, 80%, 85%, 90%, preferably 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The phrases "specifically binds to a protein" or "specifically immunoreactive with" refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires a binding moiety that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every polynucleotide sequence described herein, which encodes a protein also describes every possible silent variation, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid, which encodes a protein is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

One of skill will appreciate that many conservative variations of the fusion proteins and nucleic acid which encode the fusion proteins yield essentially identical products. For example, due to the degeneracy of the genetic code, "silent substitutions" (i.e., substitutions of a nucleic acid sequence which do not result in an alteration in an encoded protein) are an implied feature of every nucleic acid sequence which encodes an amino acid. As described herein, sequences are preferably optimized for expression in a particular host cell used to produce the chimeric endonucleases (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

The practice of this invention can involve the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, eukaryotic cells including insect, mammalian and fungal cells (e.g., *Aspergillus niger*)

Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. *Proc. Natl. Acad. Sci. USA* 86: 1173 (1989); Guatelli et al. *Proc. Natl. Acad. Sci. USA* 87: 1874 (1990); Lomell et al. *J. Clin. Chem.* 35: 1826 (1989); Landegren et al. *Science* 241: 1077-1080 (1988); Van Brunt *Biotechnology* 8: 291-294 (1990); Wu and Wallace *Gene* 4: 560 (1989); and Barringer et al. *Gene* 89: 117 (1990). Improved methods of cloning in vitro amplified nucleic acids are described in Wallace et al., U.S. Pat. No. 5,426,039.

The term "mutating" or "mutation," as used in the context of introducing site(s) into a wild-type enzyme, refers to the deletion, insertion, or substitution of any nucleotide or amino acid residue, by chemical, enzymatic, or any other means, in a polynucleotide sequence encoding a peptide. The site for a mutation introducing a mutation may be located anywhere in the polypeptide.

Introduction

The present invention provides a class of inducibly fluorescent probes that include a fluorophore joined to a quencher through a linker moiety. The quencher is a substrate for an enzyme or it reacts with a product of an enzyme reaction. The reaction with the enzyme or enzyme product diminishes or eliminates the ability of the quencher to quench fluorescence from the fluorophore. Thus, the probes of the invention are "switchable" from non- or minimally-fluorescent ("dark") to fluorescent or more intensely fluorescent ("light") in the presence of an enzyme or enzyme reaction product.

Residing in the field of fluorescent labels, the present invention provides benefits of particular note. Fluorescent labels have the advantage of requiring few precautions in handling, and being amenable to high-throughput visualization techniques (optical analysis including digitization of the image for analysis in an integrated system comprising a computer). Exemplary labels exhibit one or more of the following characteristics: high sensitivity, high stability, low background, low environmental sensitivity and high specificity in labeling. Many fluorescent labels of use in the present invention are commercially available from the SIGMA-Aldrich chemical company (Saint Louis, Mo.), Invitrogen (Carlsbad, Calif.), R&D systems (Minneapolis, Minn.), GE Healthcare (Piscataway, N.J.), BD Biosciences (San Jose, Calif.), Chem Genes Corp. (Wilmington, Wash.),—Glen Research, Inc. (Sterling, Va.),—, Fluka Chemica—Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify a commercially available fluorophore compounds to arrive at the desired fluorescent label.

The probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

Probes

The present invention provides dual labeled probes that include both a fluorophore and a quencher that quenches fluorescence emission from the fluorophore. Inducibly fluorescent dual labeled probes that include both a fluorophore and a quencher attached by a "linker" are exemplified in the art by an array of dual labeled nucleic acid probes. The nucleic acid probes are of use in conjunction with a variety of nucleic acid amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. See, for example, Cardullo, R., et al., *Proc. Natl. Acad. Sci. USA*, 85:8790-8794 (1988); Dexter, D. L., *J. Chem. Physics*, 21:836-850 (1953); Hochstrasser, R. A., et al., *Biophysical Chemistry*, 45:133-141 (1992); Selvin, P., *Methods in Enzymology*, 246:300-334 (1995); Steinberg, I., *Ann. Rev. Biochem.*, 40:83-114 (1971); Stryer, L., *Ann. Rev. Biochem.*, 47:819-846 (1978); Wang, G., et al., *Tetrahedron Letters*, 31:6493-6496 (1990); Wang, Y., et al., *Anal. Chem.*, 67:1197-1203 (1995); Debouck, C., et al., in supplement to *nature genetics*, 21:48-50 (1999); Rehman, F. N., et al., *Nucleic Acids Research*, 27:649-655 (1999); Cooper, J. P., et al., *Biochemistry*, 29:9261-9268 (1990); Gibson, E. M., et al., *Genome Methods*, 6:995-1001 (1996); Hochstrasser, R. A., et al., *Biophysical Chemistry*, 45:133-141 (1992); Holland, P. M., et al., *Proc Natl. Acad. Sci USA*, 88:7276-7289 (1991); Lee, L. G., et al., *Nucleic Acids Rsch.*, 21:3761-3766 (1993); Livak, K. J., et al., *PCR Methods and Applications*, Cold Spring Harbor Press (1995); Vamosi, G., et al., *Biophysical Journal*, 71:972-994 (1996); Wittwer, C. T., et al., *Biotechniques*, 22:176-181 (1997); Wittwer, C. T., et al., *Biotechniques*, 22:130-38 (1997); Giesendorf, B. A. J., et al., *Clinical Chemistry*, 44:482-486 (1998); Kostrikis, L. G., et al., *Science*, 279:1228-1229 (1998); Matsuo, T., *Biochemica et Biophysica Acta*, 1379:178-184 (1998); Piatek, A. S., et al., *Nature Biotechnology*, 16:359-363 (1998); Schofield, P., et al., *Appl. Environ. Microbiology*, 63:1143-1147 (1997); Tyagi S., et al., *Nature Biotechnology*, 16:49-53 (1998); Tyagi, S., et al., *Nature Biotechnology*, 14:303-308 (1996); Nazarenko, I. A., et al., *Nucleic Acids Research*, 25:2516-2521 (1997); Uehara, H., et al., *Biotechniques*, 26:552-558 (1999); D. Whitcombe, et al., *Nature Biotechnology*, 17:804-807 (1999); Lyamichev, V., et al., *Nature Biotechnology*, 17:292 (1999); Daubendiek, et al., *Nature Biotechnology*, 15:273-277 (1997); Lizardi, P. M., et al., *Nature Genetics*, 19:225-232 (1998); Walker, G., et al., *Nucleic Acids Res.*, 20:1691-1696 (1992); Walker, G. T., et al., *Clinical Chemistry*, 42:9-13 (1996); and Compton, J., *Nature*, 350:91-92 (1991).

The probes of use in practicing the methods of the present invention include a quencher that is a substrate for an enzyme or is reactive with a product of an enzymatic reaction. The structure of the quencher is altered by the enzyme or enzyme product, reducing or eliminating its ability to quench fluorescence from the fluorophore. An exemplary probe design is shown below:

F-L-Q in which F is a fluorophore, Q is a quencher and L is a linker moiety joining the fluorophore and quencher. The components are linked together by the reaction of reactive functional groups of complementary reactivity. Thus, in another exemplary embodiment, the probes of the invention have the formula:

F—X-L-$X^1$-Q in which X and $X^1$ are linking members that are formed by the reaction of a reactive group of the fluorophore with a reactive group of complementary reactivity of the linker, and a reactive group of the quencher with a reactive group of complementary reactivity of the linker, respectively. Exemplary identities for X and $X^1$ are moities that are essentially stable under physiologically relevant conditions, e.g., $NR^{10}$, O, S, $C(O)NR^{10}$, $OC(O)NR^{10}$, $C(O)$, $P(O)O_2O^-$, in which $R^{10}$ is selected from a bond, substituted or unsubstituted alkyl and substituted or unsubstituted heteroalkyl moieties. Other linking members will be apparent to those of skill in the art.

In other exemplary embodiments dual enzymatic activities are queried using one probe. In such exemplary embodiments a probe having the one or more of the following structures is useful:

$F^1$—$X^1$-L-$X^2$-Q-$X^3$-$L^2$-$X^4$—$F^2$ and

—$X^1$-$L^1$-$X^2$—F—$X^3$-$L^2$-$X^4$-Q wherein $X^2$, $X^3$, $X^4$ are linking members as X and $X^1$ above, $F^1$ and $F^2$ are flourophores, Q is a quencher, and $L^1$ and $L^2$ are linker moieties as above.

Some exemplary fluorophore-quencher pairs of use in the present invention are shown in Table 1.

TABLE 1

| Quencher | Dyes |
| --- | --- |
| BHQ-1 | BODIPY 493/503 |
|  | Alexa 488 |
|  | FAM |
|  | Oregon Green |
|  | TET |
|  | JOE |
|  | Cal Fluor ® Orange 560 ™ |
| BHQ-2 | Alexa 546 |
|  | TAMRA |
|  | BODIPY 581/591 |
|  | Rhodamine Red-X |
|  | Cy3.5 |
|  | Alexa 594 |
|  | Cal Fluor ® Red 610 ™ |

The chemical formulae below, set forth structures of exemplary probes of the invention. The scheme shows the product of the reduction of a probe that includes BHQ-1; the quencher is reduced to an aniline derivative.

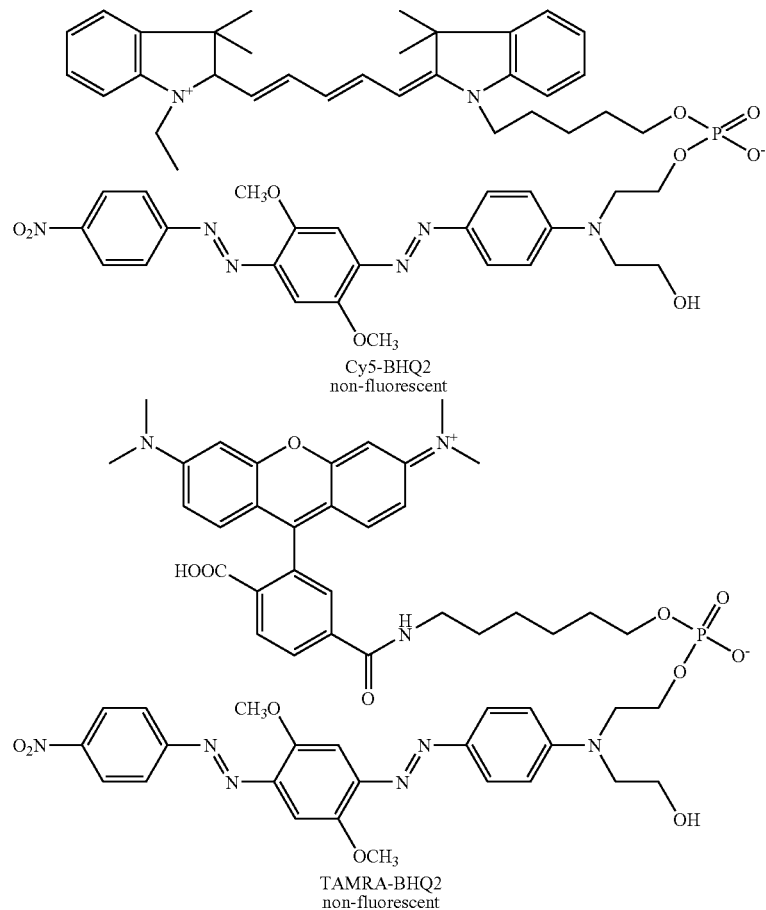

Cy5-BHQ2
non-fluorescent

TAMRA-BHQ2
non-fluorescent

-continued

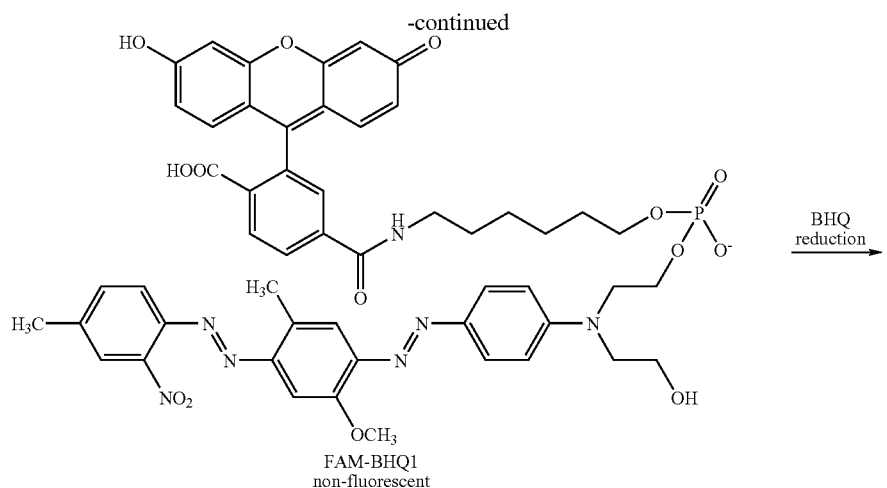

FAM-BHQ1
non-fluorescent

BHQ reduction →

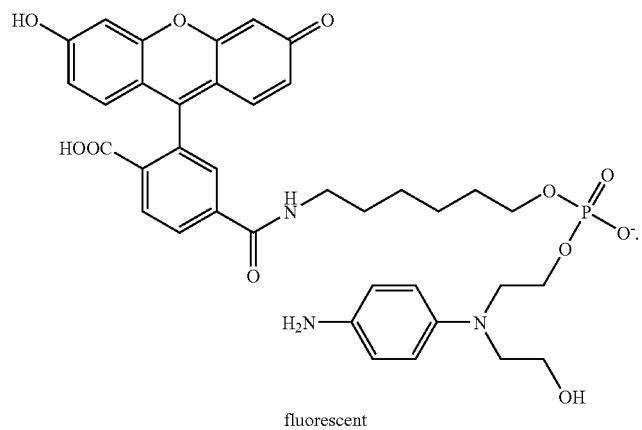

fluorescent

As shown in Scheme 1 below, selective enzymatic reduction, e.g., by an azoreductase, of an azo-based quencher moiety in operative proximity with a fluorophore on a probe produces a fluorescent signal that is of use in assays with research and diagnostic applications.

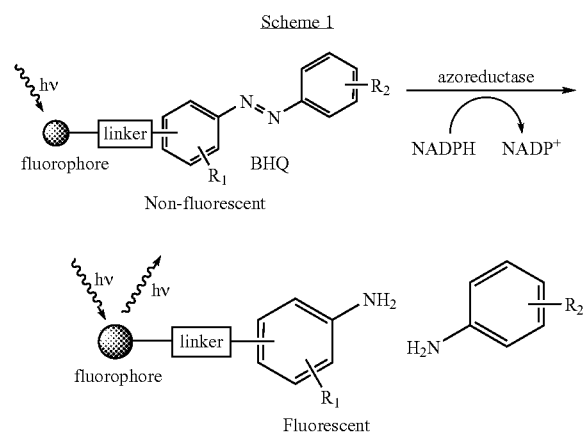

Each of the components of the probes is discussed in greater detail below.

The Fluorophore

The probes of use in the present invention can be prepared with substantially any fluorophore that is a donor for a selected quencher. There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive functional groups, which are components of a linker, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a linker.

TABLE 2

Suitable moieties that can be selected
as donors or acceptors in donor-acceptor energy transfer pairs 4-acetamido-4'-isothiocyanatostilbene-2,2'disulfonic acid
acridine and derivatives:
　acridine
　acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
　7-amino-4-methylcoumarin (AMC, Coumarin 120)
　7-amino-4-trifluoromethylcouluarin (Coumaran 151)
xanthene dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[diN-methylamino]naphthalene-1-sulfonyl chloride
(DNS, dansylchloride)
4-(4'-diN-methylaminophenylazo)benzoic acid (DABCYL)
4-diN-methylaminophenylazophenyl-4'-isothiocyanate (DABITC)
eosin and derivatives:
　eosin
　eosin isothiocyanate
erythrosin and derivatives:
　erythrosin B
　erythrosin isothiocyanate
ethidium
fluorescein and derivatives:
　5-carboxyfluorescein (FAM)
　5-(4,6-dichlorotriazin-2-yl)aminofluorescein (DTAF)
　2',7'-dimethoxy-4'5'-dichloro-6-carboxyfluorescein (JOE)
　fluorescein
　fluorescein isothiocyanate
　QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
　pyrene
　pyrene butyrate
　succinimidyl 1-pyrene butyrate
quantum dots
Reactive Red 4 (Cibacron ™ Brilliant Red 3B-A)
rhodamine and derivatives:
　6-carboxy-X-rhodamine (ROX)
　6-carboxyrhodamine (R6G)
　lissamine rhodamine B sulfonyl chloride rhodamine (Rhod)
　rhodamine B
　rhodamine 123
　rhodamine X isothiocyanate
　sulforhodamine B TABLE 2-continued Suitable moieties that can be selected
as donors or acceptors in donor-acceptor energy transfer pairs sulforhodamine 101
　sulfonyl chloride derivative of sulforhodamine 101 (Texas Red)
　N,N,N',N'-tetramethyl-6-carboxyrhodamine (TAMRA)
　tetramethyl rhodamine
　　tetramethyl rhodamine isothiocyanate (TRITC)
　riboflavin
　rosolic acid
　terbium chelate derivatives Additional fluorophores of use in practicing the present invention are disclosed in commonly owned U.S. Provisional Patent Application No. 60/542,137, filed Feb. 4, 2004; and U.S. patent application Ser. No. 10/824,175, filed Apr. 13, 2004.

The Quencher

Quenchers of use in practicing the invention include those that undergo a reaction that diminishes their ability to quench fluorescence from the fluorophore component of the probe.

An exemplary quencher includes an azo bond within its framework. An array of azo-based quenchers has been engineered to efficiently block the emission of most fluorophores (see, for example, WO 01/86001 and U.S. Pat. No. 6,699, 975). The azo-based quenchers serve as substrates for a bacterial azoreductase. Upon reduction of the azo bond, the quenching ability is disrupted and the fluorescence of the neighboring fluorophore(s) restored (Scheme 1).

In a preferred embodiment, the quencher includes a diazo bond that covalently links two members that are independently selected from substituted or unsubstituted aryl, substituted or unsubstituted heteroaryl, and substituted or unsubstituted unsaturated alkyl.

Exemplary quenchers according to the Black Hole Quencher ("BHQ") format that are of use in the present invention include quenchers having the formulae:

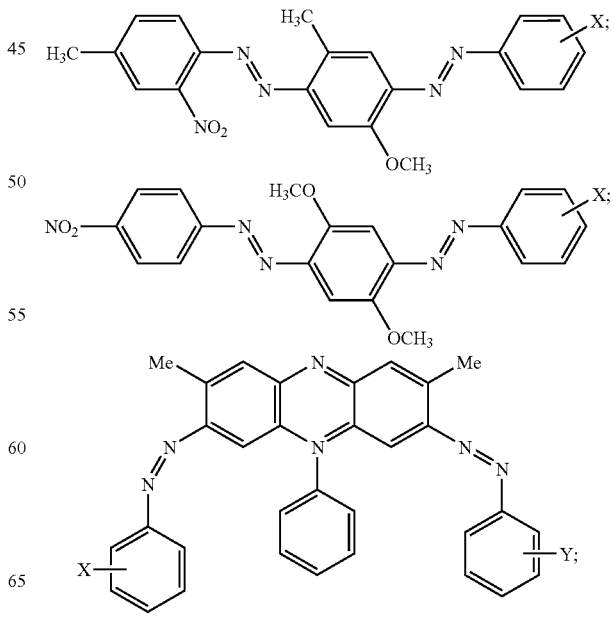

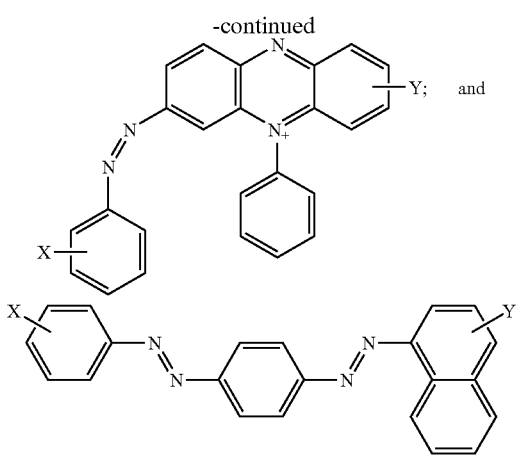

wherein, X and Y represent members independently selected from H, a reactive functional group, a bond to a carrier molecule (e.g., a targeting moiety), a linker bound to a carrier molecule, a solid support, a linker attached to a solid support, a bond to a fluorophore, and a linker bound to a fluorophore. At least one member selected from X and Y preferably is other than H.

In another embodiment, the quencher is a quinone, such as an anthraquinone. An exemplary anthraquinone quencher has the formula:

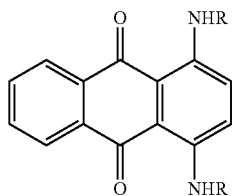

in which the "R" groups are selected from substituted or unsubstituted alkyl, substituted or unsubstituted aryl and substituted or unsubstituted heteroaryl moieties. See, May et al., *Chem. Comm.*, 970-971 (2003).

The reduction of quinones by quinone reductases is known in the art. See, for example, He et al., *Proc. Nat. Acad. Sci. USA* 98:926-931 (2001).

The Linker

Probes of the present invention include a linker moiety to which both the fluorophore and quencher are joined. The linker can be selected from any desirable structure for a particular application and it is well within the abilities of one of skill in the art to select and appropriate linker moiety. The only practical restriction on the linker structure is that it is generally preferred that the linker be of a length and conformation that allows the quencher and the fluorophore to come within operative proximity prior to the reaction of the quencher with the enzyme or enzyme reaction product.

Exemplary linkers are selected from substituted or unsubstituted alkyl, a substituted or unsubstituted heteroalkyl, a substituted or unsubstituted aryl, substituted or unsubstituted heterocycloalkyl or a substituted or unsubstituted heteroaryl moiety. The linker groups can be hydrophilic (e.g., tetraethylene glycol, hexaethylene glycol, polyethylene glycol) or they can be hydrophobic (e.g., hexane, decane, etc.). Certain exemplary linkers include substituted or unsubstituted $C_6$-$C_{30}$ alkyl groups, polyols (e.g., glycerol), polyethers (e.g., poly(ethyleneglycol)), polyamines, amino acids (e.g., polyaminoacids), saccharides (e.g., polysaccharides), and species that include quaternary amines, phosphate and phosphate ester moieties and combinations thereof.

In yet a further embodiment, a linker group used in the probes of the invention is provided with a group that can be cleaved to release the probe from a species to which it is bound, e.g., solid support, antibody, enzyme, or to release a moiety that is a component of the probe, e.g., the fluorophore, quencher, drug moiety, targeting moiety, carrier molecule and the like from the linker component. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) linker arms is commercially available from suppliers such as Pierce. Exemplary cleaveable groups are those cleaved by light, e.g., nitrobenzyl derivatives, phenacyl groups, benzoin esters; hydrolysis, e.g., esters, carbonates; changes in pH, etc.

In an exemplary embodiment, the linker imparts water-solubility to the probe and has the formula:

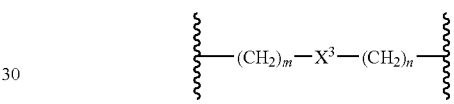

wherein $X^3$ is a member selected from $CH_2$, $NR^{10}$, O, S, $C(O)NR^{10}$, $OC(O)NR^{10}$, $P(O)O_2O^-$, O, $^+N(R^{10})_2$, $NR^{10}$, $OC(O)NR^{10}$, $C(O)NR^{10}$, and $O(CH_2CH_2)_s$, in which s is an integer from 1 to 10. $R^{10}$ is H, substituted or unsubstituted alkyl, or substituted or unsubstituted heteroalkyl. The water-solubility of probes that include this linker arm is greater than an otherwise identical probe that does not include "X".

The linker may also be the bond that is cleaved by the enzymatic reaction, for example, an azo bond. In an exemplary embodiment, the cleavage of the azo bond converts a non-fluorescent compound into a fluorescent species by separating a fluorescent (or "profluorescent") component of a molecule from a second component of the molecule that quenches the fluorescence of the component. An example of the cleavage of a non-fluorescent, azo-containing compound, leading to production of a fluorescent species is set forth below.

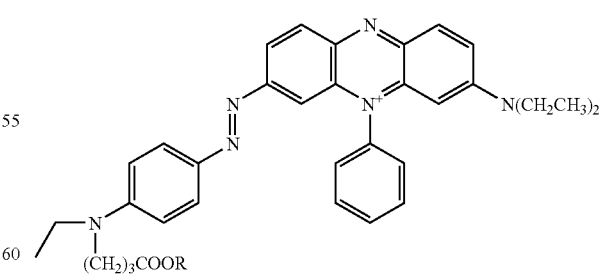

(Janus Green)
Nonfluorescent

↓ Azoreductase

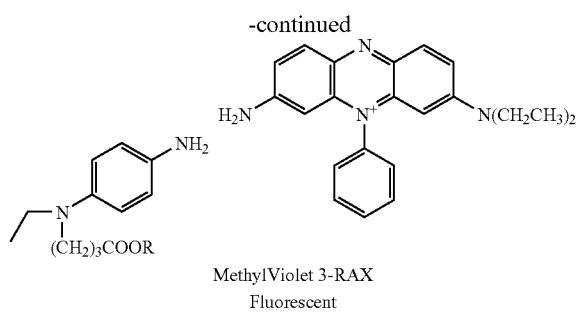

MethylViolet 3-RAX
Fluorescent

In the example above, the azo bond is cleaved by the action of a reductase. The invention also encompasses embodiments in which a bond is cleaved by another enzyme or a chemical reductant, e.g., ascorbic acid. As will be appreciated by those of skill in the art, the aryl rings of the moieties set forth above are optionally substituted with one or more substituents for aryl or heteroaryl moieties as set forth herein.

Reactive Functional Groups

The probes of the invention are assembled by reaction of complementary reactive functional groups on the linker, fluorophore and quencher moieties. Typically, the linking member that is the reaction product formed from the two reactive functional groups is stable under physiologically relevant conditions. Exemplary compounds of the invention, particularly those probes that are designed to be conjugated to another species, bear a reactive functional group, which can be located at any position on the probe molecule through which the probe is conjugated to the other species.

Reactive groups and classes of reactions useful in practicing the present invention are generally those that are well known in the art of bioconjugate chemistry. Currently favored classes of reactions are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and derivatives thereof including, but not limited to activated esters, e.g., N-hydroxysuccinimide esters, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;

(b) hydroxyl groups, which can be converted to esters, sulfonates, phosphoramidates, ethers, aldehydes, etc.

(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, allowing derivatization via formation of carbonyl derivatives, e.g., imines, hydrazones, semicarbazones or oximes, or via such mechanisms as Grignard addition or alkyllithium addition;

(f) sulfonyl halide groups for reaction with amines, for example, to form sulfonamides;

(g) thiol groups, which can be converted to disulfides or reacted with acyl halides, for example;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble or utilize the probe or a conjugate thereof. Alternatively, a reactive functional group can be protected from participating in a selected reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In addition to those embodiments in which a probe of the invention is attached directly to another species, e.g., carrier molecule, solid support, targeting moiety, the probe can also be attached by indirect means. In an exemplary embodiment, a ligand molecule (e.g., biotin) is generally covalently bound to the probe species. The ligand then binds to another molecule (e.g., streptavidin) molecule, which is covalently bound to a species that is a target species for an analysis. Other assay formats that rely on the indirect binding of two or more assay components are known to those of skill in the art.

The probes, or enzymes reactive towards the probes, can be immobilized on substantially any polymer, biomolecule, or solid or semi-solid material having any useful configuration. Moreover, any conjugate comprising one or more probe (or enzyme) can be similarly immobilized. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high cross-linked polystyrene (1000 Å) are particularly preferred.

A large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (Biosearch Technologies, Inc.), ion exchange media (Aldrich), functionalized membranes (e.g., —COOH membranes; Asahi Chemical Co., Asahi Glass Co., and Tokuyama Soda Co.), and the like.

Moreover, for applications in which an appropriate solid support is not commercially available, a wide variety of reaction types are available for the functionalization of a solid support surface. For example, supports constructed of a plastic such as polypropylene, can be surface derivatized by chromic acid oxidation, and subsequently converted to hydroxylated or aminomethylated surfaces. The functionalized support is then reacted with a xanthene dye of the invention of complementary reactivity, such as a xanthene dye of the invention active ester, acid chloride or sulfonate ester, for example. Supports made from highly crosslinked divinylbenzene can be surface derivatized by chloromethylation and subsequent functional group manipulation. Additionally, functionalized substrates can be made from etched, reduced polytetrafluoroethylene.

When the support is constructed of a siliceous material, such as glass, the surface can be derivatized by reacting the surface Si—OH, SiO—H, and/or Si—Si groups with a functionalizing reagent.

In an exemplary embodiment, wherein the substrate is made from glass, the covalent bonding of the reactive group to the glass surface is achieved by conversion of groups on the substrate's surface by a silicon-modifying reagent such as:

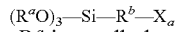

where $R^a$ is an alkyl group, such as methyl or ethyl, $R^b$ is a linking group between silicon and reactive group $X^a$. Silane derivatives having halogens or other leaving groups other than alkoxy groups are also useful in the present invention. Exemplary linking groups include those that include substituted or unsubstituted alkyl and substituted or unsubstituted heteroalkyl groups.

In another preferred embodiment, the reagent used to functionalize the solid support provides for more than one reactive group per each reagent molecule. Using reagents, such as the compound below, each reactive site on the substrate surface is, in essence, "amplified" to two or more functional groups:

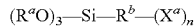

where $R^a$ is an alkyl group (e.g., methyl, ethyl), $R^b$ is a linking group between silicon and $X^a$, $X^a$ is a reactive group or a protected reactive group, and n is an integer between 2 and 50, more preferably between 2 and 20. The amplification of a probe of the invention by its attachment to a silicon-containing substrate is intended to be exemplary of the general concept of amplification. This amplification strategy is equally applicable to other aspects of the invention in which a probe of the invention is attached to another molecule or solid support.

A number of siloxane functionalizing reagents can be used, for example:
1. Hydroxyalkyl siloxanes (Silylate surface, functionalize with diborane, and $H_2O_2$ to oxidize to the alcohol)
    a. allyl trichlorosilane→→3-hydroxypropyl
    b. 7-oct-1-enyl trichlorchlorosilane→→8-hydroxyoctyl;
2. Diol (dihydroxyalkyl) siloxanes (silylate surface and hydrolyze to diol)
    a. (glycidyl trimethoxysilane→(2,3-dihydroxypropyloxy)propyl;
3. Aminoalkyl siloxanes (amines requiring no intermediate functionalizing step);
    a. 3-aminopropyl trimethoxysilane→aminopropyl
4. Dimeric secondary aminoalkyl siloxanes
    a. bis(3-trimethoxysilylpropyl)amine→bis(silyloxylpropyl)amine.

It will be apparent to those of skill in the art that an array of similarly useful functionalizing chemistries is available when support components other than siloxanes are used. Thus, for example alkyl thiols (e.g., self-assembled monolayers), functionalized as discussed above in the context of siloxane-modifying reagents, can be attached to metal films and subsequently reacted with a xanthene dye of the invention to produce the immobilized compound of the invention.

Exemplary groups of use for $R^b$ in the above described embodiments of the present invention include, but are not limited to, substituted or unsubstituted alkyl (e.g., substituted or unsubstituted arylalkyl, alkylamino, alkoxy), substituted or unsubstituted aryl (e.g., substituted or unsubstituted arylalkyl, aryloxy and aryloxyalkyl), acyl (e.g., acylamino, acyloxy), mercapto, saturated or unsaturated cyclic hydrocarbyl, substituted or unsubstituted heteroaryl (e.g., substituted or unsubstituted heteroarylalkyl), substituted or unsubstituted heterocycloalkyl, and combinations thereof.

In another exemplary embodiment, a species conjugated to a probe of the invention is immobilized within a matrix, such as an acrylamide matrix, e.g., "acrydite" (see, Rehman et al., *Nucleic Acids Research,* 27: 649-655 (1999)).

Irreversibly Internalized Probes

In another embodiment, the invention provides probes that include a group, typically a lipophilic group, that facilitates the internalization of the probe into a cell. The facilitating group is preferably linked to the remainder of the probe through a bond that is cleaved by normal cellular processes, e.g., esterases, lipases, etc. Alternatively, the group can be cleaved by a change in pH, such as that which occurs on going from an extracellular environment to an endocytotic vacuole (e.g., pH 7 to pH 4). The facilitating group can also be cleaved by an intracellular process that is induced. An exemplary probe and its differing states are set forth in the example below.

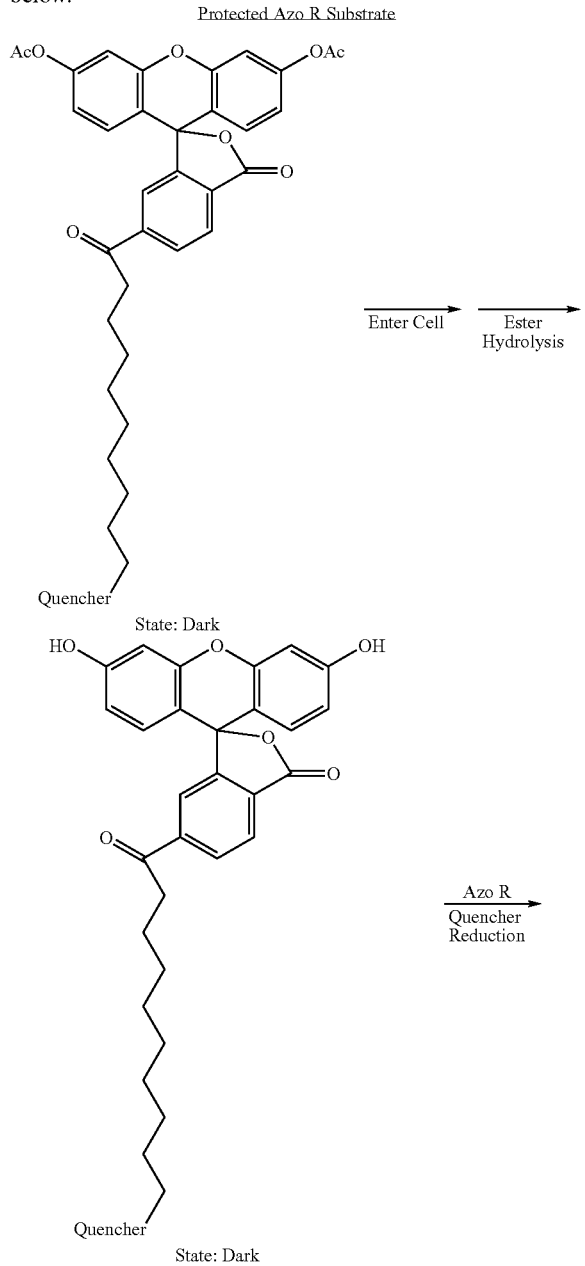

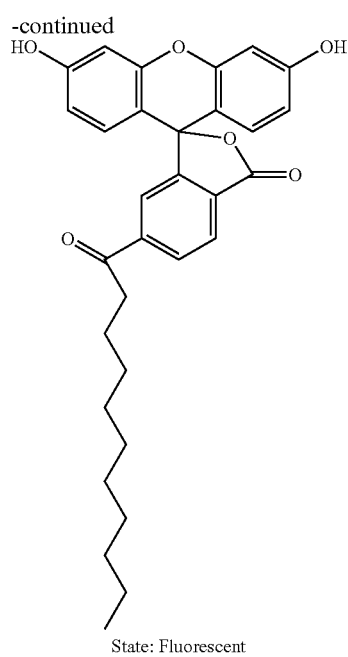

State: Fluorescent

In the example above, the probe penetrates the cell wall, becoming internalized in the cell. The acetyl esters are hydrolyzed by intracellular components, trapping the negatively charged probe within the cell. The azo bond of the probe is subsequently cleaved, leaving behind a moiety (not shown) that does not efficiently quench the fluorophore, thereby producing a fluorescent product. The presence of the product in the cell can be confirmed by microscopic or spectroscopic methods, confocal microscopy, cell sorting, etc.

In another exemplary embodiment, as shown below, a side-chain carboxylic acid ester is cleaved, trapping the probe within the cell and the azo bond is cleaved, producing a fluorescent signal.

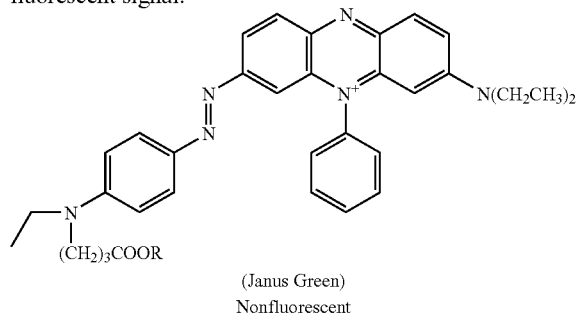

(Janus Green)
Nonfluorescent

↓ Neutral Dye enters Cell

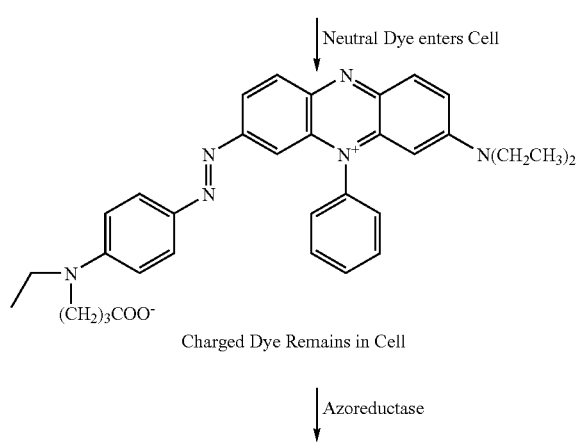

Charged Dye Remains in Cell

↓ Azoreductase

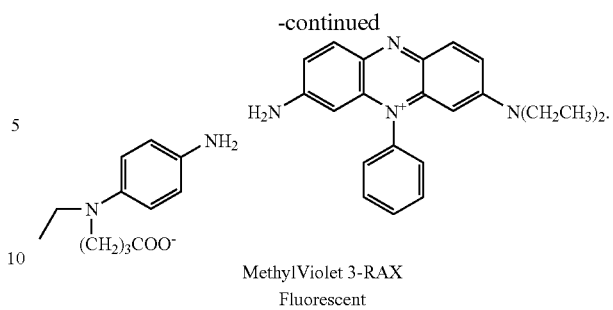

MethylViolet 3-RAX
Fluorescent

As will be appreciated by those of skill in the art, the probes according to the present invention are not limited to the cleavable groups or the number of cleavable groups shown in the examples above. Moreover, probes based upon an array of combinations of aryl, conjugated, unsaturated alkyl or heteroaryl groups linked by an azo, or other cleavable bond are within the scope of the present invention. The alkyl, aryl and heteroaryl moieties are optionally subsituted with one or more subsitutuent, such as those described in the definition section herein.

Microarrays

The present invention also provides microarrays of various formats that are of use in performing an assay of the invention. In an exemplary microarray, a probe of the invention, or a species to which a probe of the invention is conjugated is immobilized and used to interrogate an assay sample for the presence of an enzyme or other species that reacts with the quencher of the probe, disrupting its ability to quench fluorescence from a fluorophore. In another exemplary format, the enzyme or a species to which the enzyme is attached is immobilized.

Moreover, the invention provides methods of interrogating microarrays using probes or methods of the invention. In an exemplary embodiment, the enzyme is conjugated to a targeting moiety that binds to an immobilized analyte. The analyte and targeting moiety are contacted under conditions appropriate for them to interact, immobilizing the targeting agent-enzyme construct on the microarray. Following any necessary subsequent steps, e.g., washing, buffer change, etc., the probe is added to the microarray. Regions of fluorescence confirm the presence of the analyte. The assay can be run in a somewhat different, but analogous manner, when the targeting moiety is conjugated to the probe. In this case, the microarray is contacted with the enzyme, giving rise to fluorescence in those regions where the analyte is immobilized.

The microarrays of the invention are better understood by reference to nucleic acid microarrays. Nucleic acid microarrays consisting of a multitude of immobilized nucleic acids are revolutionary tools for the generation of genomic information, see, Debouck et al., in supplement to *Nature Genetics*, 21:48-50 (1999). The discussion that follows focuses on the use of a xanthene dye of the invention in conjunction with nucleic acid microarrays. This focus is intended to be illustrative and does not limit the scope of materials with which this aspect of the present invention can be practiced.

Exemplary microarrays comprise n regions of identical or different species (e.g., nucleic acid sequences, bioactive agents). In a preferred embodiment, n is a number from 2 to 100, more preferably, from 10 to 1,000, and more preferably from 100 to 10,000. In a still further preferred embodiment, the n regions are patterned on a substrate as n distinct locations in a manner that allows the identity of each of the n locations to be ascertained.

Methods of preparing microarrays are well known in the art. See, for example, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990); Pirrung et al., U.S. Pat. No. 5,143,854, issued 1992; and also by Fodor et al., *Science,* 251: 767-773 (1991); Southern et al. *Genomics,* 13: 1008-1017 (1992); Khrapko, et al., *DNA Sequence,* 1: 375 -388 (1991); Kleinfield et al., *J. Neurosci.* 8: 4098-120 (1998); Kumar et al., *Langmuir* 10: 1498-511 (1994); Xia, Y., *J. Am. Chem. Soc.* 117: 3274-75 (1995); and Hickman et al., *J. Vac. Sci. Technol.* 12: 607-16 (1994).

The Enzymes

Acquisition of Enzyme Coding Sequences

In the following sections, the preparation of enzymes that act either directly or indirectly on quenchers is exemplified by reference to acquiring a wild type or recombinant azoreductase, or a fusion protein that has azoreductase activity. The focus on azoreductases is for clarity of illustration and should not be interpreted as limiting the scope of the invention. Those of skill in the art will appreciate that the techniques described below are generally applicable to other enzymes that react directly or indirectly with a quencher. An exemplary nucleic acid coding sequence and PCR primers are shown in FIG. 9. FIG. 10 provides an alignment between the nucleic acid sequence and an azoreductase encoded by the sequence.

General Recombinant Technology

This invention relies on routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of the cloned wild-type reductase genes, polynucleotide encoding mutant reductase, and synthetic oligonucleotides can be verified after cloning using, e.g., the chain termination method for sequencing double-stranded templates of Wallace et al., *Gene* 16: 21-26 (1981).

Cloning and Subcloning of a Wild-Type Azoreductase Coding Sequence

A number of polynucleotide sequences encoding a wild-type azoreductase, e.g., AY422207, AY165002, AY150311, AF466104, AB071368, AB071367, AB071366, AB032601, have been determined and can be obtained from a commercial supplier.

The rapid progress in the studies of the genome of various species has made possible a cloning approach where a DNA sequence database can be searched for any gene segment that has a certain percentage of sequence homology to a known nucleotide sequence, such as one encoding a previously identified enzyme. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a cDNA or genomic library using a synthetic probe may be necessary to obtain a larger gene.

Alternatively, a nucleic acid sequence encoding a desired enzyme can be isolated from a cDNA or genomic DNA library using standard cloning techniques such as polymerase chain reaction (PCR), where homology-based primers can often be derived from a known nucleic acid sequence encoding a reductase. Most commonly used techniques for this purpose are described in standard texts, e.g., Sambrook and Russell, supra.

cDNA libraries suitable for obtaining a coding sequence for a desired enzyme, e.g., reductase may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full length polynucleotide sequence encoding the wild-type enzyme from the cDNA library. A general description of appropriate procedures can be found in Sambrook and Russell, supra.

A similar procedure can be followed to obtain a full length sequence encoding a wild-type enzyme, e.g., any one of the GenBank Accession Nos. mentioned above, from a genomic library. Genomic libraries are commercially available or can be constructed according to various art-recognized methods. In general, to construct a genomic library, the DNA is first extracted from a culture where the desired enzyme is likely to be found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science,* 196: 180-182 (1977). Colony hybridization is carried out as described by Grunstein et al., *Proc. Natl. Acad. Sci. USA,* 72: 3961-3965 (1975).

Based on sequence homology, degenerate oligonucleotides can be designed as primer sets and PCR can be performed under suitable conditions (see, e.g., White et al., *PCR Protocols: Current Methods and Applications,* 1993; Griffin and Griffin, *PCR Technology,* CRC Press Inc. 1994) to amplify a segment of nucleotide sequence from a cDNA or genomic library. Using the amplified segment as a probe, the full length nucleic acid encoding a wild-type enzyme is obtained.

Upon acquiring a nucleic acid sequence encoding a wild-type enzyme, the coding sequence can be subcloned into a vector, for instance, an expression vector, so that a recombinant wild-type enzyme can be produced from the resulting construct. Further modifications to the wild-type enzyme coding sequence, e.g., nucleotide substitutions, may be subsequently made to alter the characteristics of the molecule.

Modification of Nucleic Acids for Preferred Codon Usage in a Host Organism

The polynucleotide sequence encoding an enzyme can be further altered to coincide with the preferred codon usage of a particular host. For example, the preferred codon usage of one strain of bacterial cells can be used to derive a polynucleotide that encodes a mutant enzyme of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell. U.S. Pat. No. 5,824,864, for example, provides the frequency of codon usage by highly expressed genes exhibited by dicotyledonous plants and monocotyledonous plants.

At the completion of modification, the mutant enzyme coding sequences are verified by sequencing and are then subcloned into an appropriate expression vector for recombinant production in the same manner as the wild-type enzyme.

Expression and Purification of the Enzyme

Following sequence verification, the enzyme of the present invention can be produced using routine techniques in the field of recombinant genetics, relying on the polynucleotide sequences encoding the polypeptide disclosed herein.

Expression Systems

To obtain high level expression of a nucleic acid encoding an enzyme of the present invention, one typically subclones a polynucleotide encoding the enzyme into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the wild-type or mutant enzyme are available in, e.g., E. coli, Bacillus sp., Salmonella, and Caulobacter. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the enzyme in host cells. A typical expression cassette thus contains a promoter operably linked to the nucleic acid sequence encoding the enzyme and signals required for efficient polyadenylation of the transcript, ribosome binding sites, and translation initiation and termination. The nucleic acid sequence encoding the enzyme is typically linked to a cleavable signal peptide sequence to promote secretion of the enzyme by the transformed cell. Such signal peptides include, among others, the signal peptides from tissue plasminogen activator, insulin, and neuron growth factor, and juvenile hormone esterase of Heliothis virescens. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The identity of the expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the enzyme under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., a reductase mutant of the present invention) is desired, the expression vector further comprises a sequence encoding a secretion signal, such as the E. coli OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., Gene 39: 247-254 (1985), U.S. Pat. Nos. 6,160,089 and 6,436,674.

As discussed above, a person skilled in the art will recognize that various conservative substitutions can be made to any wild-type or mutant enzyme or its coding sequence while still retaining the activity of the enzyme. Moreover, modifications of a polynucleotide coding sequence may also be made to accommodate preferred codon usage in a particular expression host without altering the resulting amino acid sequence.

Transfection Methods

Standard transfection methods are used to produce bacterial, mammalian, yeast, insect, or plant cell lines that express large quantities of the enzyme, which are then purified using standard techniques (see, e.g., Colley et al., J. Biol. Chem. 264: 17619-17622 (1989); Guide to Protein Purification, in Methods in Enzymology, vol. 182 (Deutscher, ed., 1990)).

Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the mutant enzyme.

Detection of Expression of Enzyme in Host Cells

After the expression vector is introduced into appropriate host cells, the transfected cells are cultured under conditions favoring expression of the enzyme. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a desired enzyme in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with an enzyme, e.g., an azoreductase of use in the present invention, such as a polypeptide having the amino acid sequence of SEQ ID NO:2 (e.g., Harlow and Lane, *Antibodies, A Laboratory Manual*, Chapter 14, Cold Spring Harbor, 1988; Kohler and Milstein, *Nature*, 256: 495-497 (1975)). Such techniques rely on antibody preparation by selecting antibodies with high specificity against the mutant enzyme or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.*; 6: 511-519 (1976). More detailed descriptions of preparing antibody against the enzyme of the present invention and conducting immunological assays detecting the enzyme are provided in a later section.

Purification of Recombinantly Produced Enzyme

Once the expression of a recombinant enzyme in transfected host cells is confirmed, the host cells are then cultured in an appropriate scale for the purpose of purifying the recombinant polypeptide.

Purification of Recombinantly Produced Mutant Enzyme from Bacteria

When the enzymes of the present invention are produced recombinantly by transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of the immunologically and/or biologically active protein of interest. After solubilization, the protein can be separated from other bacterial proteins by standard separation techniques. For further description of purifying a recombinant protein from a bacterial inclusion body, see, e.g., Patra et al., *Protein Expression and Purification* 18: 182-190 (2000).

Alternatively, it is possible to purify recombinant polypeptides, e.g., an azoreductase, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard Protein Separation Techniques for Purification

When a recombinant polypeptide, e.g., the azoreductase of the present invention, is expressed in host cells in a soluble form, its purification can follow the standard protein purification procedure described below.

Solubility Fractionation

Often as an initial step, and if the protein mixture is complex, an initial salt fractionation can separate many of the unwanted host cell proteins (or proteins derived from the cell culture media) from the recombinant protein of interest, e.g., a mutant enzyme of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a mutant enzyme. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The proteins of interest (such as the mutant enzyme of the present invention) can also be separated from other proteins on the basis of their size, net surface charge, hydrophobicity, or affinity for ligands. In addition, antibodies raised against the enzyme can be conjugated to column matrices and the enzyme immunopurified. All of these methods are well known in the art.

It will be apparent to one of skill that chromatographic techniques can be performed at any scale and using equipment from many different manufacturers (e.g., GE Healthcare).

Immunoassays for Detection of Enzyme Expression

To confirm the production of a recombinant enzyme, immunological assays may be useful to detect in a sample the expression of the polypeptide. Immunological assays are also useful for quantifying the expression level of the recombinant enzyme. Antibodies against a recombinant enzyme are necessary for carrying out these immunological assays.

Production of Antibodies Against the Enzyme

Methods for producing polyclonal and monoclonal antibodies that react specifically with an immunogen of interest are known to those of skill in the art (see, e.g., Coligan, *Current Protocols in Immunology* Wiley/Greene, NY, 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., a mutant enzyme of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

When desired, antibodies capable of specifically recognizing a mutant enzyme of the present invention can be tested for their cross-reactivity against the wild-type enzyme and thus distinguished from the antibodies against the wild-type protein. For instance, antisera obtained from an animal immunized with the enzyme can be run through a column on which the wild-type enzyme is immobilized. The portion of the antisera that passes through the column recognizes only the mutant enzyme and not the wild-type enzyme. Similarly, monoclonal antibodies against a mutant enzyme can also be screened for their exclusivity in recognizing only the mutant but not the wild-type human growth enzyme.

Polyclonal or monoclonal antibodies that specifically recognize only the mutant enzyme of the present invention but not the wild-type enzyme are useful for isolating the mutant protein from the wild-type protein, for example, by incubating a sample with a mutant enzyme-specific polyclonal or monoclonal antibody immobilized on a solid support.

Immunoassays for Detecting Mutant Enzyme Expression

Once antibodies specific for a mutant enzyme of the present invention are available, the amount of the polypeptide in a sample, e.g., a cell lysate, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

Labeling in Immunoassays

Immunoassays often utilize a labeling agent to specifically bind to and label the binding complex formed by the antibody and the target protein. The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase, and others commonly used in an ELISA), and colorimetric labels such as colloidal gold or colored glass or plastic (e.g., polystyrene, polypropylene, latex, etc.) beads.

In some cases, the labeling agent is a second antibody bearing a detectable label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111: 1401-1406 (1973); and Akerstrom, et al., *J. Immunol.*, 135: 2589-2542 (1985)).

Immunoassay Formats

Immunoassays for detecting a target protein of interest (e.g., a reductase) from samples may be either competitive or noncompetitive. Noncompetitive immunoassays are assays in which the amount of captured target protein is directly measured. In one preferred "sandwich" assay, for example, the antibody specific for the target protein can be bound directly to a solid substrate where the antibody is immobilized. It then captures the target protein in test samples. The antibody/target protein complex thus immobilized is then bound by a labeling agent, such as a second or third antibody bearing a label, as described above.

In competitive assays, the amount of target protein in a sample is measured indirectly by measuring the amount of an added (exogenous) target protein displaced (or competed away) from an antibody specific for the target protein by the target protein present in the sample. In a typical example of such an assay, the antibody is immobilized and the exogenous target protein is labeled. Since the amount of the exogenous target protein bound to the antibody is inversely proportional to the concentration of the target protein present in the sample, the target protein level in the sample can thus be determined based on the amount of exogenous target protein bound to the antibody and thus immobilized.

In some cases, western blot (immunoblot) analysis is used to detect and quantify the presence of an enzyme in the samples. The technique generally comprises separating sample proteins by gel electrophoresis on the basis of molecular weight, transferring the separated proteins to a suitable solid support (such as a nitrocellulose filter, a nylon filter, or a derivatized nylon filter) and incubating the samples with the antibodies that specifically bind the target protein. These antibodies may be directly labeled or alternatively may be subsequently detected using labeled antibodies (e.g., labeled sheep anti-mouse antibodies) that specifically bind to the antibodies against a mutant enzyme.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.*, 5: 34-41 (1986)).

Introducing Mutations into an Enzyme Sequence

From an encoding polynucleotide sequence, e.g., SEQ ID NO:1, the amino acid sequence of a wild-type azoreductase can be determined. Subsequently, this amino acid sequence may be modified to alter one or more of the protein's properties, e.g., substrate specificity, reactivity, stability, solubility in a selected medium, and the like, by introducing one or more mutations at various locations in the amino acid sequence.

Although direct modification of an amino acid residue within an enzyme's polypeptide sequence may be suitable to introduce or alter an enzyme property, more frequently, the enzyme property is introduced or altered by mutating the polynucleotide sequence encoding the enzyme. This can be achieved by using any of known mutagenesis methods, some of which are discussed below.

A variety of mutation-generating protocols are established and described in the art. See, e.g., Zhang et al., *Proc. Natl. Acad. Sci. USA*, 94: 4504-4509 (1997); and Stemmer, *Nature*, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)), or direct chemical synthesis of gene.

The Methods

In another aspect of the embodiment, the present invention provides a method for detecting a target species in an assay mixture or other sample. The following discussion is generally relevant to the assays described herein. This discussion is intended to illustrate the invention by reference to certain exemplary embodiments and should not be interpreted as limiting the scope of probe structures and assay types encompassed by the present invention. Other assay formats utilizing the concepts of the invention will be apparent to those of skill in the art.

In an exemplary embodiment, the invention provides a reporter gene assay, such as those useful in the study of gene regulatory elements. A reporter gene construct for use in these assays contains one or more gene that encodes and enzyme, e.g., a reductase, that acts on a quencher of fluorescence energy to reduce the ability of the quencher to quench fluorescence emission from the fluorophore. The reporter protein acts directly or indirectly on a quencher of fluorescence emission to reduce its ability to reduce the emission. The activity of the transcribed reporter protein, or quantification of the expressed protein, provides an indirect measurement of gene expression. Reporter gene assays enable the identification of sequences and factors that control gene expression at the transcriptional and post-transcriptional levels. Bronstein et al, *BioTechniques* 17: 172 (1994).

In another exemplary embodiment, there is also provided a multiple gene assay according to a format of the invention. In single reporter gene assays with poor sensitivity it is difficult to distinguish negative results caused by the lack of expression or low level assay sensitivity. This problem can be overcome with assays of greater sensitivity. Multiple gene assays are commonly used to provide controls for efficiency of transfection. In such assays, cells are transfected with a mixture of two separate plasmids, each having a different reporter gene. The expression of one reporter gene is controlled by different regulatory regions being studied while the other reporter gene, acting as a control, is generally constitutively expressed by a standard promoter or enhancer. The activity of the experimental reporter enzyme is normalized to the activity of the control reporter enzyme.

The method of this invention also provides methods of quantifying the product of one or more reporter genes by measuring multiple enzyme activities in a single aliquot of cell extract or cell culture medium. One such method comprises (a) quantifying the activity of a first reporter enzyme in an aliquot of the cell extract or cell culture medium by measuring the light signal produced by degradation of a quencher; (b) quantifying the activity of a second reporter enzyme in the aliquot of the cell extract or cell culture medium by measuring the light signal produced by degradation of a second quencher. The method may further include the step of (c) quantifying the activity of a third reporter enzyme in the aliquot of the cell extract by measuring the light signal produced by degradation of a third quencher.

Each quantification may be sequentially performed on the same aliquot of sample extract. Alternatively, due the ability provided by the present invention to engineer the enzyme-substrate specificity for the enzyme-quencher pair, two or more of the quantifications may be performed essentially simultaneously.

In another embodiment, the method of measuring products of two or more reporter genes further comprises decreasing the real or apparent activity of one or more of the reporter enzymes prior to subsequently quantifying the activity another reporter enzyme.

The invention also provides a system for detecting the products of one or more reporter gene in an aliquot of a target compound. The system includes the reagents for quantifying each of the reporter enzymes, wherein at least one of the reporter enzymes, or a product of the enzyme reacts with the quencher of a probe of the invention.

In addition to reporter gene assay formats that indicate the presence of the reporter protein itself, the invention provides assays for a substance that activates the protein. For example, when the reporter protein is an NADPH-dependent azoreductase, an increase in fluorescence due to azoreductase degradation of the quencher in a dual labeled probe can be used to confirm the presence of NADPH in a sample. The NADPH may be added to the assay mixture or, alternatively, it may be produced by a protein in the assay mixture. In the latter case, the azoreductase serves as a reporter for species involved in the synthesis of NADPH, or species in the NADP-NADPH pathway.

In another embodiment, the assay detects an enzyme that activates or synthesizes a non-protein agent that reacts with the quencher of the probe. For example, an assay mixture may include an ester-masked reducing agent (e.g., an ascorbic acid ester) and a cell expressing an esterase. The esterase cleaves the ester, unmasking the active reducing group which reacts with the quencher. The ability of the quencher to quench fluorescence from the fluorophore is diminished, resulting in an increase in detectable fluorescence.

In another exemplary embodiment, the present invention provides an assay for a target substance. The target substance may be directly or indirectly (e.g. a specific binding interaction such as with an antibody linked to the enzyme for which the quencher is a substrate. The method of the invention allows the use of any enzyme that reacts directly or indirectly with the quencher. An exemplary enzyme is a reductase, such as a quinone- or azo-reductase.

The invention also provides immunoassays, such as enzyme linked immunoassays (ELISA), and assay formats described in the prededing sections relevant to detecting protein expression. ELISA assays are used in all areas of clinical and life science research to detect disease markers including proteins, hormones and antibodies. In an industrial setting, such assays may be used to detect contaminants and for quality control by monitoring for the presence of a specific molecule. In a simple "sandwich" immunoassay, an antibody is adsorbed onto a microtiter plate. The sample is added to the plate and any reactive antigen binds to the antibody layer. Washing removes all the unbound sample and contaminants, and then the antigen is detected by addition of a polyclonal antibody that also binds the antigen, now affixed to the plate. This antibody can be crosslinked to a probe of the invention, a reporter enzyme, such as that of the invention, or labeled with an epitope such as biotin that can then be detected by avidin crosslinked to a reporter enzyme or probe. Use of the second, or "secondary", antibody tends to reduce background and therefore increase the sensitivity of the assay. In an "antigen-down" immunoassay, the antigen is present on the plate, and any antibodies in the sample bind the antigen. The presence of antibodies adhered to the plate is reported by a labeled secondary antibody. The antibody can be labeled with a probe or enzyme. Western blotting is another essential tool for protein analysis that relies on enzyme-labeled antibodies for detection and would similarly benefit from the addition of a new reporter to the existing repertoire.

Multiplex Analyses

Currently, the ability to simultaneously screen for multiple antigens makes an assay faster and less expensive to run, however, each antigen requires a unique detection method. Although progress has been made in developing substrates for existing reporters with a variety of fluorescence signatures, novel and orthogonal reporter systems are needed to keep up with demand for increasingly complex analyses, e.g., proteomic analysis. Ideally, a new reporter system also accommodates a range of pre-fluorescent substrates to be readily compatible with existing methods.

Thus, in another exemplary embodiment, the probes of the invention are utilized as a component of a multiplex assay for detecting one or more target species in a mixture. In such "multiplexing" applications, strictly segregated substrate specificities and fluorophore emission wavelengths are preferred.

The present invention provides a panel of quenched fluorophores with resolved emission wavelengths that can each be unquenched by the action of an enzyme, e.g., azoreduction, or by a reaction product of an enzyme, e.g., ascorbic acid. For example, BHQ1 effectively quenches the green emitting dye FAM and the more red-shifted JOE. Moreover, a panel of probes has been developed in which green fluorescent protein (GFP) is multiplexed with a BHQ1-JOE azoreductase probe. Alternately, the red protein phycoerythrin is utilized in a probe in combination with a BHQ1-FAM azoreductase assay.

The methods of the invention are of use in multiplex analyses of numerous analytes including, but not limited to, the detection and/or quantification of substantially any species, including, for example, whole cells, viruses, proteins (e.g., enzymes, antibodies, receptors), glycoproteins, lipoproteins, subcellular particles, organisms (e.g., *Salmonella*), nucleic acids (e.g., DNA, RNA, and analogues thereof), polysaccharides, lipopolysaccharides, lipids, fatty acids, non-biological polymers and small molecules (e.g., toxins, drugs, pesticides, metabolites, hormones, alkaloids, steroids).

Molecular Imaging

In another embodiment, the invention provides in vivo assays, such as in vivo molecular imaging. For in vivo application of azoreductases in mammalian cells, the enzymatic activity must be orthogonal to endogenous reductases. Thus far, no mammalian azoreductases have been cloned. However, there is evidence to suggest that the liver may possess azoreductase activity. See, for example, Huang et al., *J. Biol. Chem.* 254: 3930-3934 (1979); Stoddart et al., *Biochem. Pharmacol.* 43: 2227-2235 (1992); and Martin et al., *Carcinogenesis* 2: 307-312 (1981). The mammalian enzymes appear to be significantly less permissive with respect to substrate structure than the bacterial enzymes and they are also strongly inhibited by the presence of oxygen. Where endogenously expressed reductases are a concern, the background azoreduction can be examined by incubation of untransfected cells in culture with quenched substrates and monitoring fluorescence at the expected wavelength.

This embodiment of the invention is based on the discovery that in vivo fluorochrome signals from a variety of probes, such as specific targeted molecular probes, e.g., probes targeted for specific enzyme activities or DNA sequences, can be localized in three dimensions in deep tissues and can be quantitated with high sensitivity using a specially designed imaging system for this purpose and relying on self-calibrated image reconstruction and new algorithms to extract molecular maps.

General principles of fluorescence, optical image acquisition, and image processing can be applied in the practice of the invention. For a review of optical imaging techniques, see, e.g., Alfano et al., *Ann. NY Acad. Sci.* 820: 248-270 (1997).

An imaging system useful in the practice of this invention typically includes three basic components: (1) a light source, (2) a means for separating or distinguishing fluorescence emissions from light used for fluorochrome excitation, and (3) a detection system. See, for example, Weissleder et al., United States Patent Application 2003/0219383.

The light source provides monochromatic (or substantially monochromatic) near infrared light. The light source can be a suitably filtered white light, i.e., bandpass light from a broadband source. For example, light from a 150-watt halogen lamp can be passed through a suitable bandpass filter commercially available from Omega Optical (Brattleboro, Vt.). In some embodiments, the light source is a laser. See, e.g., Boas et al., *Proc. Natl. Acad. Sci. USA* 91: 4887-4891 (1994); Ntziachristos et al., *Proc. Natl. Acad. Sci. USA* 97: 2767-2772 (2000); Alexander, *J. Clin. Laser Med. Surg.* 9: 416-418 (1991). Information on near infrared lasers for imaging can be found at http://www.imds.com.

A high pass filter (e.g., 700 nm) can be used to separate fluorescence emissions from excitation light. A suitable high pass filter is commercially available from Omega Optical.

In general, the light detection system can be viewed as including a light gathering/image forming component and a light detection/image recording component. Although the light detection system may be a single integrated device that incorporates both components, the light gathering/image forming component and light detection/image recording component will be discussed separately.

A particularly useful light gathering/image forming component is an endoscope. Endoscopic devices and techniques which have been used for in vivo optical imaging of numerous tissues and organs, including peritoneum (Gahlen et al., *J. Photochem. Photobiol. B* 52: 131-135 (1999)), ovarian cancer (Major et al., *Gynecol. Oncol.* 66: 122-132 (1997)), colon (Mycek et al., *Gastrointest. Endosc.* 48: 390-394 1998); Stepp et al., *Endoscopy* 30: 379-386 (1998)) bile ducts (Izuishi et al., *Hepatogastroenterology* 46: 804-807 (1999)), stomach (Abe et al., *Endoscopy* 32: 281-286 (2000)), bladder Kriegmair et al., *Urol. Int.* 63: 27-31 (1999) Riedl et al., *J. Endourol.* 13: 755-759 (1999)), and brain (Ward, *J. Laser Appl.* 10: 224-228 (1998)) can be employed in the practice of the present invention.

Other types of light gathering components useful in the invention are catheter-based devices, including fiber optics devices. Such devices are particularly suitable for intravascular imaging. See, e.g., Tearney et al., *Science* 276: 2037-2039 (1997); *Proc. Natl. Acad. Sci. USA* 94: 4256-4261.

Still other imaging technologies, including phased array technology (Boas et al., *Proc. Natl. Acad. Sci. USA* 91: 4887-4891 (1994); Chance, *Ann. NY Acad. Sci.* 838: 29-45 (1998)), diffuse optical tomography (Cheng et al., *Optics Express* 3: 118-123 (1998); Siegel et al., *Optics Express* 4: 287-298 (1999)), intravital microscopy (Dellian et al., *Br. J. Cancer* 82: 1513-1518 (2000); Monsky et al, *Cancer Res.* 59: 4129-4135 (1999); Fukumura et al., *Cell* 94: 715-725 (1998)), and confocal imaging (Korlach et al., *Proc. Natl. Acad. Sci. USA* 96: 8461-8466 (1999); Rajadhyaksha et al., *J. Invest. Dermatol.* 104: 946-952 (1995); Gonzalez et al., *J. Med.* 30: 337-356 (1999)) can be employed in the practice of the present invention.

Any suitable light detection/image recording component, e.g., charge coupled device (CCD) systems or photographic film, can be used in the invention. The choice of light detection/image recording will depend on factors including type of light gathering/image forming component being used. Selecting suitable components, assembling them into a near infrared imaging system, and operating the system is within ordinary skill in the art.

In another exemplary embodiment, the invention provides a method for performing fluorescence-mediated molecular tomography (FMT) using an inducible fluorescence dual labeled probe, as described herein. Instrumentation systems for FMT are known in the art. For example, see Ntziachristos et al., United States Patent Application 2004/0015062. Briefly, an appropriated system for performing FMT includes a light source (e.g., a near infrared or visible light source) to provide incident light; a multipoint incident illumination array to direct light into an object, e.g., an animal or human patient, from two or more separate excitation points; multiple optic fibers to transmit light from the light source to each point in the multipoint incident illumination array; a multipoint detection array to collect light, e.g., fluorescent light, emitted from the object from two or more separate collection points; a two-dimensional emitted light array to transmit light emitted from the object to a detector; multiple optic fibers to transmit light from each collection point to a corresponding point on the two-dimensional emitted light array; and a detector to detect and convert light emitted from each point of the two-dimensional emitted light array into a digital signal corresponding to the light emitted from the object.

The system can further include a processor that processes the digital signal produced by the detector to provide an image on an output device. The output device can provide multiple images simultaneously. The processor can be programmed to process the digital signal by any one or combinations of: i) generating a corrected fluorescence measurement by subtracting a background signal and filter bleed-through signal from collected fluorescence measurements; ii) generating a corrected intrinsic signal measurement by subtracting a background ambient light signal from collected intrinsic signal measurements; iii) generating a self-calibrated fluorescence measurement by dividing the corrected fluorescence measurement by the corrected intrinsic measurement; iv) generating a corrected background-medium diffuse signal by subtracting the collected background ambient light signal from a collected diffuse signal; and v) generating a self-calibrated intrinsic measurement by dividing the corrected intrinsic signal measurement by the corrected background-medium diffuse signal.

The system typically also features a method for displaying i) a fluorochrome distribution and/or lifetime as resolved by vector U and/or ii) an optical molecular map corresponding to a ratio of a concentration of a molecular probe comprising a fluorophore administered to a patient to a concentration of an activated fluorophore corresponding to a specific target in the patient by: i) providing a first data set of fluorophore concentration based on intrinsic absorption; ii) providing a second data set of activated fluorophore concentration based-on fluorescence; iii) dividing the first data set by the second data set on a point-by-point basis to provide a third data set; and iv) processing the third data set to provide an optical molecular map corresponding to a ratio of a concentration of a molecular probe comprising a fluorophore to a concentration of an activated fluorophore corresponding to a specific target in the patient.

In Vitro Probe Testing

After a probe is designed and synthesized, it can be tested routinely in vitro to verify a requisite level of intramolecular fluorescence quenching before activation, and to confirm the reaction of the quencher with the enzyme or other species. Preferably, this is done by obtaining a fluorescence value for the intramolecularly quenched, fluorochrome-containing probe in a dilute buffer. This value is then compared to the fluorescence value obtained from an equimolar concentration of free fluorochrome in the same buffer, under the same fluorescence-measuring conditions. Preferably, this comparison will be done at a series of dilutions, to verify that the measurements are taking place on a linear portion of the fluorescence vs. fluorochrome concentration curve.

The molar amount of an intramolecularly-quenched fluorochrome on a probe can be determined by one of ordinary skill in the art using any suitable technique. For example, the molar amount can be determined readily by near infrared absorption measurements.

After suitable intramolecular fluorescence quenching is verified, "de-quenching," i.e., fluorescence, upon exposure to an activating enzyme also can be verified in vitro. In an exemplary procedure, fluorescence of an intramolecularly-quenched probe is measured before and after treatment with an activating enzyme.

In addition, cells grown in culture can be used routinely to test intramolecularly-quenched near infrared fluorescence probes. Probe molecules free in cell culture medium lacking an activating enzyme should be non-detectable by fluorescence microscopy. Cellular uptake should result in probe activation and a fluorescence signal from probe-containing cells. Microscopy of cultured cells thus can be used to verify that activation takes place upon uptake by a cell expressing an activating enzyme of a probe being tested. Microscopy of cells in culture is also a convenient means for determining whether activation occurs in one or more subcellular compartments.

Kits

In another aspect, the present invention provides kits containing one or more probe of the invention or a conjugate thereof. In one embodiment, a kit includes a reactive probe of the invention and directions for attaching this probe to another molecule. In another embodiment, the kit includes a probe-labeled carrier, e.g., a nucleic acid, peptide, enzyme, or antibody, and directions for using this conjugate in one or more assay format. Other formats for kits will be apparent to those of skill in the art and are within the scope of the present invention.

The materials and methods of the present invention are further illustrated by the examples that follow. These examples are offered to illustrate, but not to limit the claimed invention.

The following examples are provided by way of illustration only and not by way of limitation. Those of skill in the art will readily recognize a variety of non-critical parameters that could be changed or modified to yield essentially similar results.

EXAMPLES

Example 1

Expression Strategy for the Production of Soluble BTI1 Azoreductase

Figure 2:
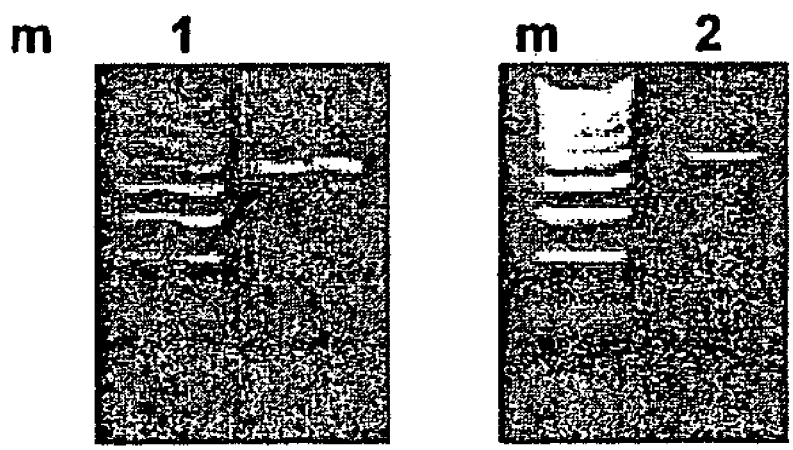
FIG. 2 is an agarose gel showing azoreductase from two different soil samples. Left lane: molecular weight markers (m), Right lane: azoreductase PCR products 1 and 2.

Based on the work of Suzuki et al, PCR primers were synthesized corresponding to a known azoreductase that incorporated sites for restriction digest (Suzuki et al., *J. Biol. Chem.* 276: 9059-9065 (2001). Samples of bacteria were cultivated from various locally available sources including soil, water and skin. Isolation of the genomic DNA from these bacteria yielded potential templates for amplifying the azoreductase sequence. Conditions were determined that permitted successful PCR (FIG. 2) of the azoreductase gene from two different soil samples using the primers synthesized at Biosearch Technologies, Inc. Sequencing of the PCR products revealed high homology to several known azoreductases. The PCR products are each approximately 530 base pairs in length, which is similar to the reported azoreductase gene from *Bacillus* sp. OY1-2.

The PCR products encoding the two putative azoreductases were ligated into the pBAD vector (Invitrogen) to provide constructs both with and without a C-terminal $His_6$-tag. The $His_6$-tag provides a means of purifying the protein on Ni resin as well as identifying the protein via western blot analysis. Appending tags has the potential to diminish enzymatic activity thus the construct without the tag was also generated. The resulting plasmids were used to transform chemically competent TOP 10 *E. Coli* cells. Selection for ampicillin resistance provided colonies possessing the azoreductase gene. Subsequent sequencing revealed that the two soil samples yielded identical azoreductase genes, and therefore one was selected for protein expression experiments.

The pBAD vector places the gene of interest under the control of an arabinose-inducible promoter. In addition, pBAD encodes a pIII signal sequence that directs expressed protein to the periplasm where it can be released by osmotic shock for ease of purification. Expression was initiated by the addition of arabinose to growing cultures of TOP10 cells. Initial experiments demonstrated that addition of arabinose results in the appearance of a new protein corresponding to the expected molecular weight of 18 kD for the azoreductase. Further experiments revealed 0.002% arabinose to be the optimal concentration for maximal expression in 4 h.

Figure 3:
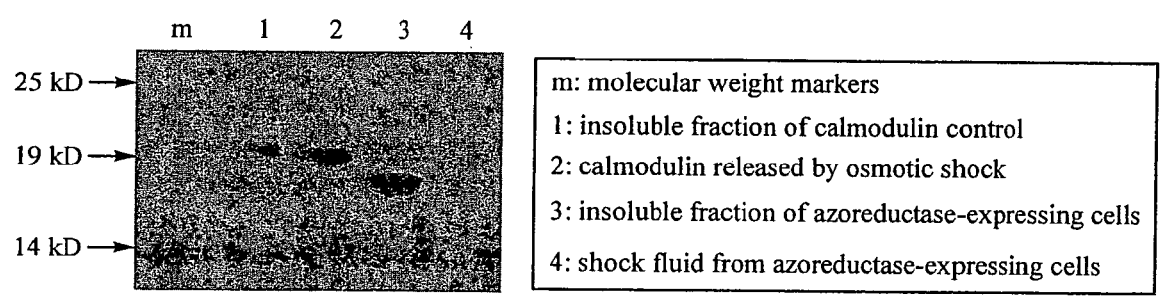
FIG. 3 is a SDS-PAGE gel showing osmotic shock of control cells expressing calmodulin (lanes 1 and 2) and cells expressing azoreductase (lanes 3 and 4).

Surprisingly, no protein was released by osmotic shock. FIG. 3 shows that induced azoreductase remains in the insoluble fraction and is not released by osmotic shock, while under the same conditions a calmodulin control is efficiently released by osmotic shock. Certain sequences result in inefficient secretion and therefore it was possible that soluble protein was formed but not secreted or produced in an insoluble, misfolded form. Complete lysis of the cell membrane was achieved using lysozyme and still no protein was found in the soluble fraction. This meant that not only was the protein misfolded (and therefore inactive) but it also retained the N-terminal pIII sequence that would have been cleaved upon secretion into the periplasm.

Figure 4:
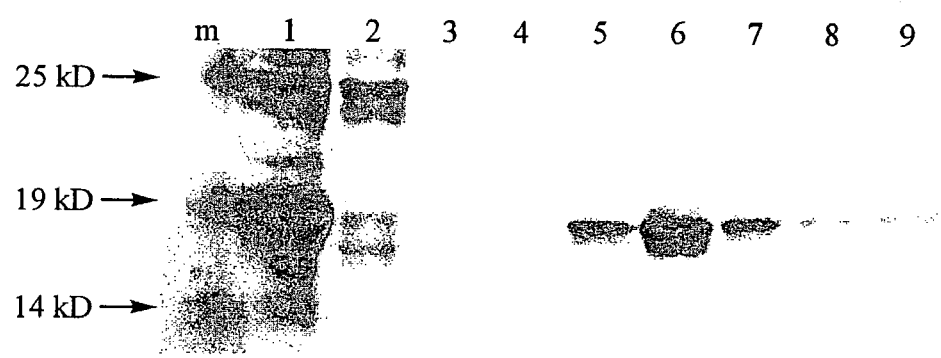
FIG. 4 is a gel showing the refolding and purification of azoreductase using ProBond Ni resin (Invitrogen).

Various conditions were examined to encourage protein folding, such as low temperature expression, increasing incubation time and minimizing arabinose levels. None of these variations produced soluble protein, so methods for solubilizing and refolding the protein were examined. Eventually, such conditions were found, allowing small amounts of soluble enzyme to be purified by Ni-affinity chromatography (FIG. 4). This process provided sufficient enzyme for activity assays.

Example 2

Alternative Expression Strategy for the Production of Soluble BTI1

Figure 5:
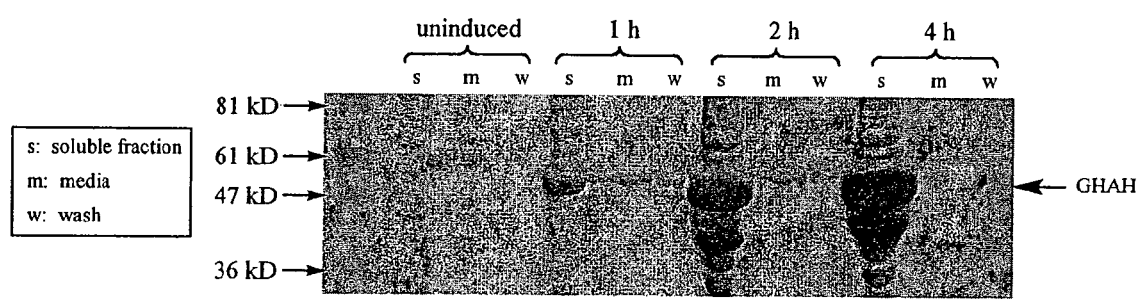
FIG. 5 is a SDS-PAGE gel showing the timecourse of GST-azoreductase fusion production.

An alternative expression strategy for the production of soluble protein was explored. The azoreductase gene was subcloned into the pET41b vector (Novagen), which incorporates an N-terminal glutathione-S-transferase (GST) sequence to enhance protein folding and solubility. After selection in *E. coli* TOP10, the plasmids were transformed into *E. coli* BL21 (DE3)pLysS cells for expression. Two separate constructs were engineered: GST-His-Azoreductase-His (GHAH) and GST-His-Azoreductase (GHA). Both produce large amounts of soluble protein upon initiation with 1 mM IPTG (a timecourse for GHAH is shown in FIG. 5).

Purification and enterokinase cleavage to remove the GST and N-terminal His sequence provides active, soluble azoreductase both with and without the C-terminal His tag.

Example 3

Three-Dimensional Structure Modeling

Figure 11:
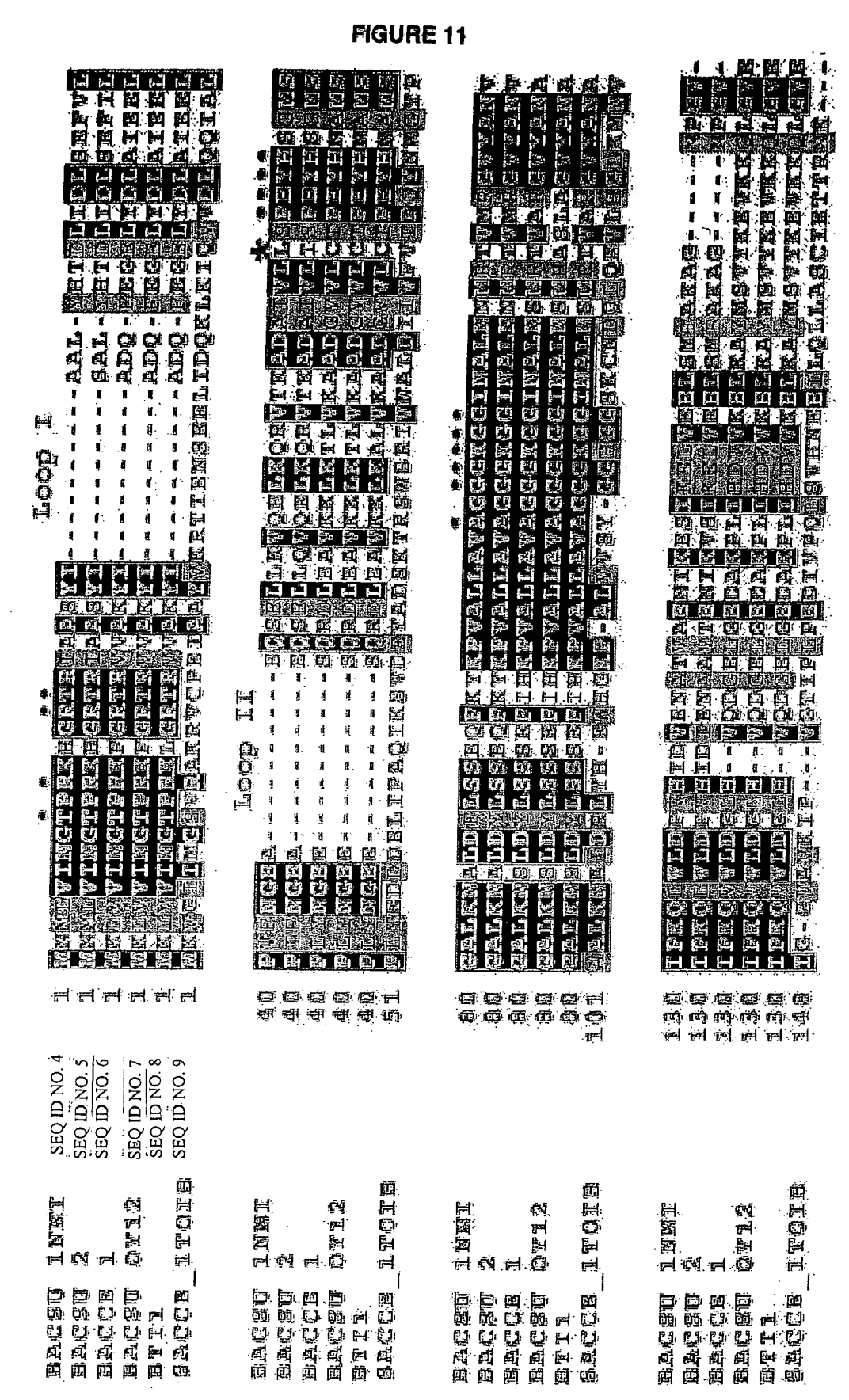

Azoreductase encoding cDNAs were isolated from soil samples as described in Example 1 (above). Sequencing of positive clones from both sources revealed one sequence, now named BTI1 (SEQ ID NO:1) with high homology to known azoreductases (FIG. 11)

A 3-D structure model of BTI1 was developed. First the nearest protein sequence neighbors were identified by using BLAST at NCBI (National Center for BioInformatics; www.ncbi.nlm.nih.gov) and aligned as shown in FIG. 11. Three dimensional crystal structures are available at RCSB PDB (Research Collaboratory for Structural Bioinformatics Protein Data Bank; www.rcsb.org/pdb/) of the related *Bacillus subtilis* homodimeric Yhda azobenzene reductase (Accession: 1NNI) and the *Saccharomyces cerevisiae* homodimeric YLR011wp NAD(P)H dependent FMN reductase (1TOI), as well as of several less related homodimeric FMN- and FAD-dependent oxidoreductases and monomeric flavodoxins. Alignment of protein sequences showed BTI1 to display 98% homology (96% identity) with *B. subtilis* OY1-2 azoR, 80% (57%) to 1NNI, and 58% (27%) to 1TOI (FIG. 11).

The alignment indicates that BTI1 stems from the *Bacillus* genus. Active site residues, identified as the FMN binding site in azobenzene reductase (1NNI), are conserved in OY1-2 azoR and BTI1 and partially in YLR011wp. FMN is bound to structurally similar sites in flavodoxins and FMN-dependent oxidoreductases. The main difference lies in the size of loops I and II (FIG. 11), which likely contributes to substrate specificity and hence is a region to be targeted for directed protein evolution. Azoreductase sequences from *Enterococcus faecalis* and *Xenophilus azovorans* are considerably removed from BTI1. However, these and other oxidoreductases with azo-reducing capacity, are useful further development of azoreductase assays.

Figure 12:
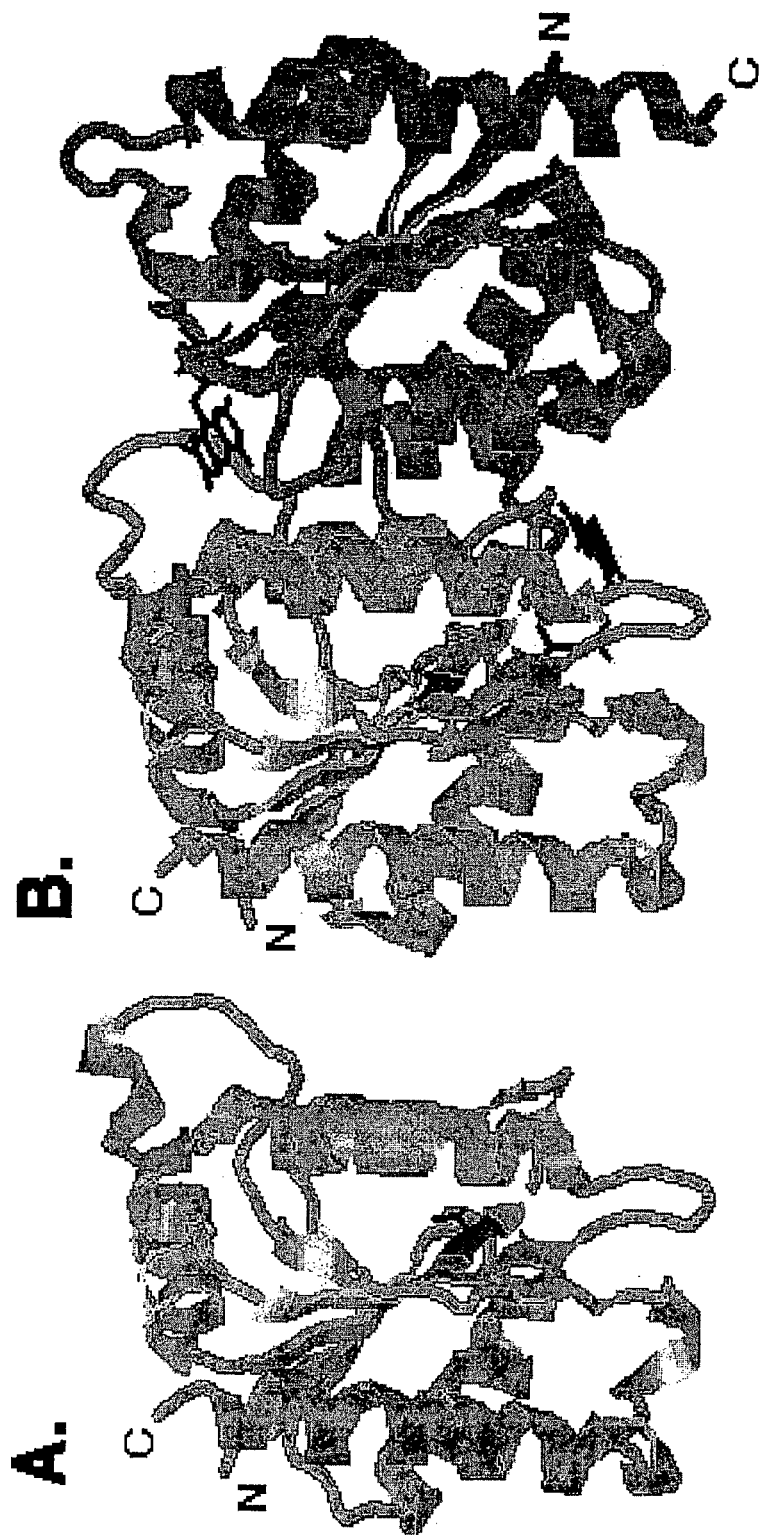
FIG. 12 Three dimensional structure model of one monomer of BTI1 built at http://swissmodel.expasy.org/ by using 1NNI and 1TOI as guides and rendered with RasMol. B) *B. subtilis* azobenzene reductase (1NNI). Chain A light gray, chain B dark gray, FMN and Cys 70 black.

Examination of the BTI1-related structures (FIG. 12) indicates that: (I) Both termini point away from the active site and are extendable with peptides for purification, immunorecognition and subcellular localization with little effect on enzymatic activity; (II) A single cysteine (Cys76) in BTI1, absent in 1NNI, is located deep within the hydrophobic core and as such unavailable for metal ion binding, SS-bridge formation or chemical crosslinking to other proteins or small molecules. C76 substituted with Ile, Val or Leu thus allows for addition of specific Cys residue(s) at either terminus for cross-linking to antibodies, etc.

Example 4

Synthesis of Quenched Probes

The following example illustrates the creation of prototype quenched probes. Three prototype quenched probes were synthesized based on three well-known fluorescent reporters: fluorescein (FAM), tamra, and Cy5. The synthesis entailed the solid phase coupling of the dye amidite to a Black Hole Quencher support using standard oligonucleotide chemistry methods. Modular synthesis of the substrates imparts versatility to the azoreductase probes and assays.

The prototype probes include a phosphate linkage that renders them water soluble for the purpose of in vitro enzymatic assays.

Chemical reduction of the three probes was carried out as a positive control for the enzymatic assay and to confirm that the residual aniline moiety does not quench fluorescence. Dithionite is known to reduce azo compounds to amines under basic conditions. Therefore this reagent was selected to model the enzymatic reaction and demonstrate the dramatic fluorescence increase that takes place upon reduction of the BHQ.

Figure 6:
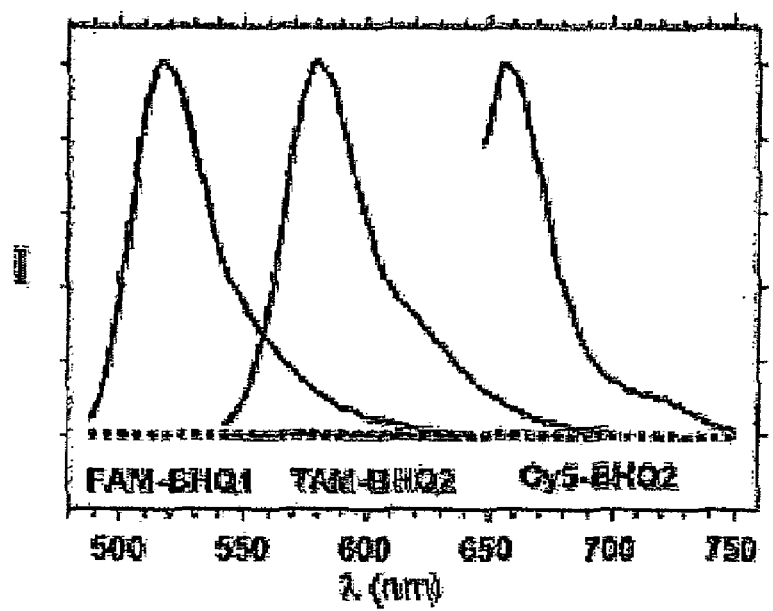
FIG. 6 is an overlay plot of fluorescence spectra of the three fluorophore-quencher conjugates before (dashed lines) and after (solid lines) reduction of the azo bond(s).
Figure 7:
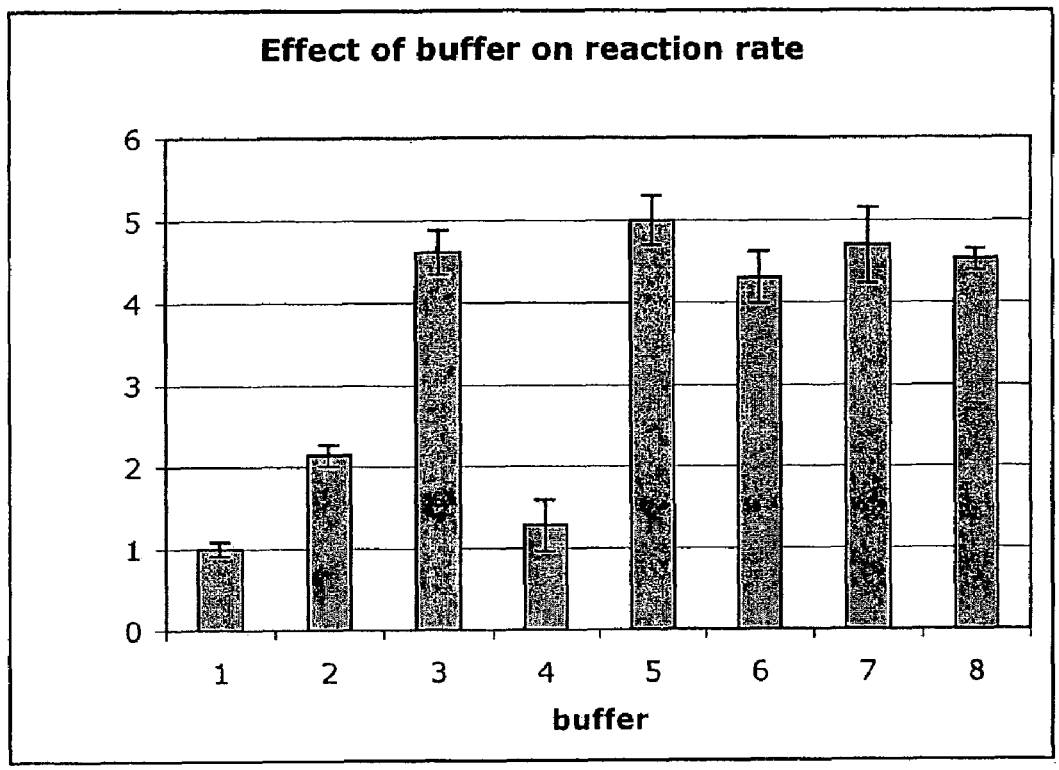
FIG. 7 are the results of an assay using refolded azoreductase with FAM-BHQ-1 as the substrate in vvarious buffers with 250 µM NADPH.

Following RP HPLC purification of the conjugates (Hamilton PRP-1 column; 0.1 N aqueous TEAA to 100% $CH_3CN$ gradient), their fluorescence was measured (Spectramax Gemini). In each case, the substrate showed virtually no measurable fluorescence, indicating quantitative quenching. Aqueous solutions of each probe were aliquoted (40 µL) into two cuvettes and 20 µL of 0.2 M dithionite, $Na_2S_2O_4$ was added to chemically reduce the BHQ moieties. PCR buffer (10× solution: 100 mM trizma hydrochloride, 500 mM KCl and 35 mM $MgCl_2$) was then added to all samples to adjust the pH to 8.5. Upon azoreduction, the following signal:background ratios were obtained for the respective dye-quencher substrates; 316 (FAM-BHQ1), 186 (TAM-BHQ2), 170 (Cy5-BHQ2). These signal enhancements are excellent and rate with the best seen with any fluorescence-quenched assay modality. Importantly, these findings confirm that the resulting aniline appendage does not negatively impact the fluorescence of the fluorophore (FIG. 6).

Example 5

Exemplary Enzymatic Assay Conditions

Figure 8:
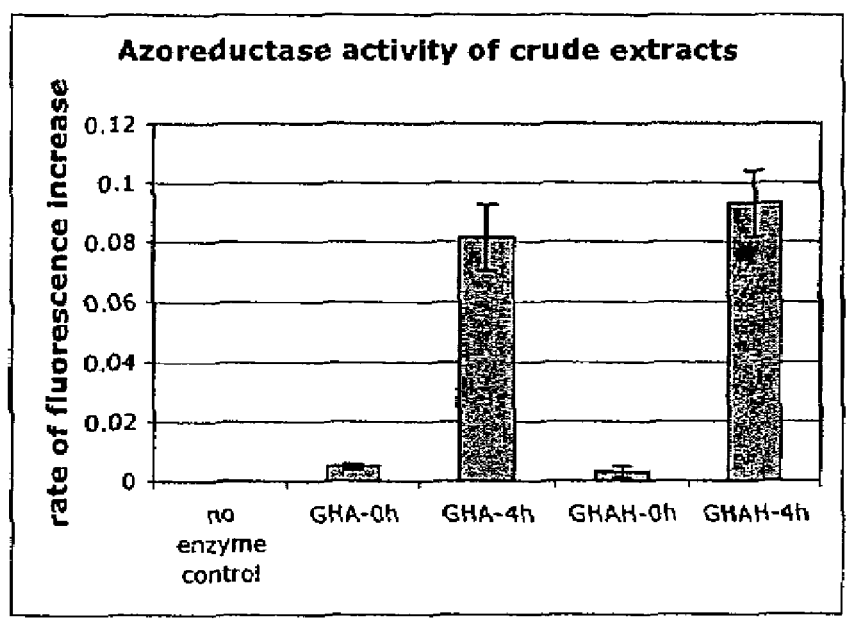
FIG. 8 are the results of an assay of GST-azoreductase fusions in crude form with FAM-BHQ-1 as the substrate in Tris buffer with 250 µM NADPH.

Initial enzymatic assay conditions were modeled on the experiments described by Suzuki and coworkers which used 20 mM phosphate buffered saline (PBS) and 250 µM NADPH. Activity was monitored using the FAM-BHQ1 probe. Repeated experiments with the refolded enzyme showed consistently high fluorescence signals over background. Different buffer conditions were examined in an effort to optimize the assay. The experiment shown in FIG. 8 demonstrates that these promising results represent a minimum level of activity under largely unoptimized conditions and with both a C-terminal (His) and N-terminal (pIII signal sequence) fusion.

Before purification of the GST fusions, the crude cell lysate was assayed for enzymatic activity. The results of this assay, indicate that the new form of the enzyme is highly active. In addition to a standard "no enzyme" control, uninduced (0 h) cell lysates were included to demonstrate low endogenous activity in the BL21(DE3)pLysS cells. The experiment was performed in triplicate and error bars represent one standard deviation. These data suggest two very promising conclusions, the first being that the enzyme can be expressed directly in a soluble active form. Second, this experiment demonstrates that the azoreductase is active as a C-terminal fusion to a full-length protein, which is critical for reporter gene applications.

Example 6
Azoreductase Reporter Gene Expression and Activity in Cultured Cells

The following example illustrates the use of azoreductase as a reporter gene in one or more mammalian cell lines.

Gene Optimization and Subcloning

BTI1 has been codon optimized for expression in mammalian cells and in *E. coli*, (internal Shine-Dalgarno and AAUAAA and transcription factor binding sequences removed, rare Arg codons substituted, the AUG start codon placed a near optimal Kozak consensus, etc.) (Gene Oracle). In this process a C70V mutant was made that eliminates the single cysteine of the BTI1 central core, and which allows for cysteine addition(s) at either terminus for crosslinking to other proteins, such as antibodies, and to small molecules.

Figure 13:
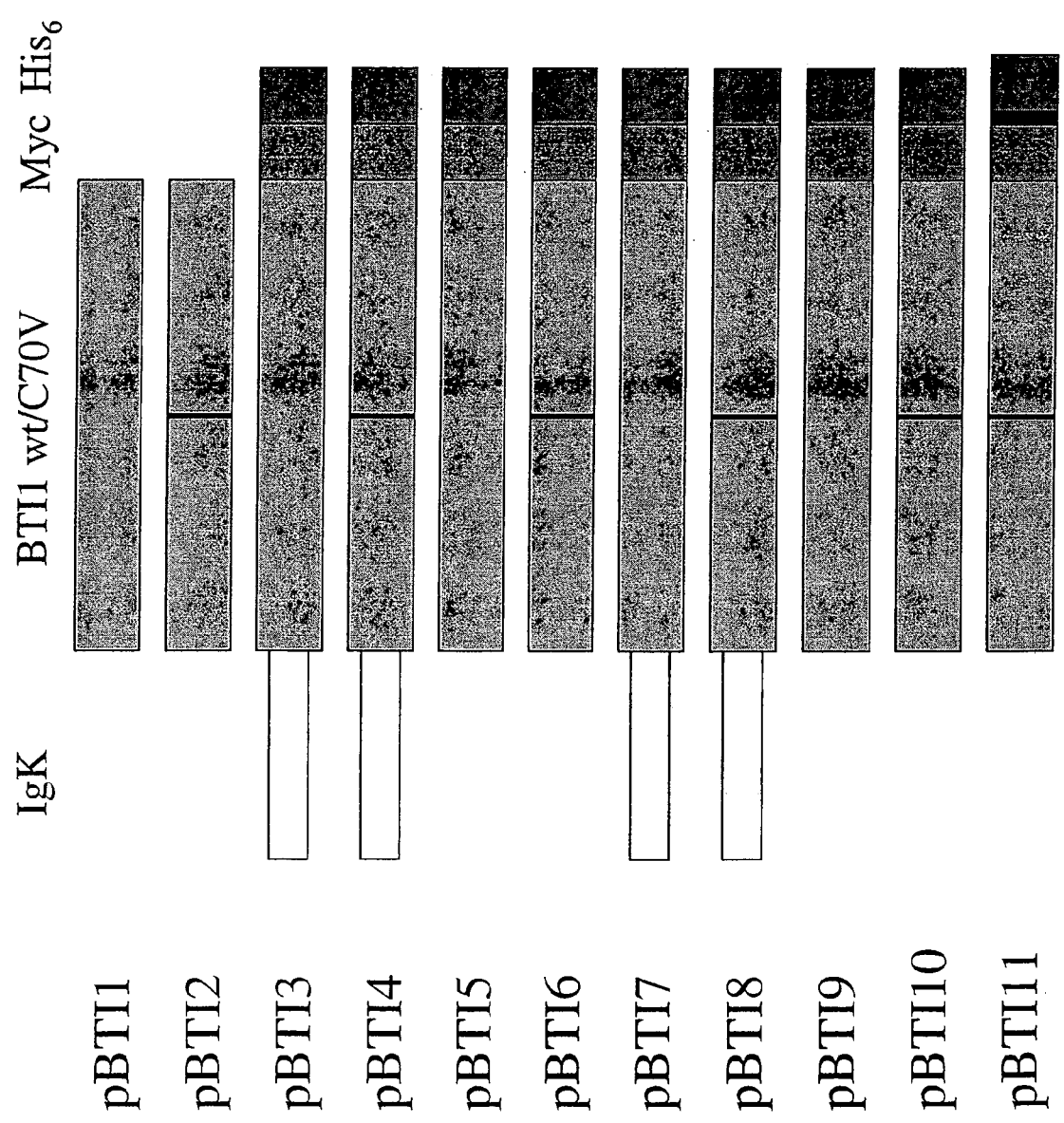
FIG. 13 Shows a schematic representation of the plasmid constructs described in Table 3. An azoreductase is expressed by each of the different plasmids. In pBTI3, pBTI4, pBTI5, and pBTI6 the base vector is pSecTag2A a shuttle plasmid for maintenance and cloning in *E. coli* and for Cytomegalovirus driven expression in animal cells. Using this vector the inserted gene is expressed as either an intra- or extracellular protein. The base vector for pBTI7, pBTI8, pBTI9, pBTI10, and pBTI11 is pET28a. The pET28 plasmid confers kanamycin resistance *E. coli* whilst providing high level expression in *E. coli* strains harboring the DE3 lysogen (T7 RNA polymerase under lactose control). Where indicated the azoreductase gene encodes either the wt: wild type; or C70V (Cys 70 Val mutant), and may be fused with myc and His6 tags for immnuorecognition and metal column affinity chromatography. Where indicated, the azoreductase is preceeded by the signal sequence form immunoglobulin Kappa chain for entry into the endoplasmic reticulum and ensuing sectretion out of the cell. Cys refers to single or multiple added Cysteins between the myc and His tags to enable specific crosslinking to other proteins, nucleic acids or small molecules.

Eight BTI1 variants were made. These variants are shown in FIG. 13, and are further described in Table 3, below.

TABLE 3

Description of pBTI1 Variant Plasmids

| Plasmid name | Backbone vector | BTI1-Variant |
|---|---|---|
| pBTI3 | pSecTag2A | wt + IgK leader + C-term myc and $His_6$ |
| pBTI4 | pSecTag2A | C70V + IgK leader + C-term myc and $His_6$ |
| pBTI5 | pSecTag2A | Wt + C-term myc and $His_6$ |
| pBTI6 | pSecTag2A | C70V + C-term myc and $His_6$ |
| pBTI7 | pET28a | wt + IgK leader + C-term myc and $His_6$ |
| pBTI8 | pET28a | C70V + IgK leader + C-term myc and $His_6$ |
| pBTI9 | pET28a | Wt + C-term myc and $His_6$ |
| pBTI10 | pET28a | C70V + C-term myc and $His_6$ |
| pBTI11 | pET28a | C70V + C-term myc, Cys and $His_6$ |

Table 3 shows plasmid constructs used and described in greater detail in Examples 6-8. The name of the constructs are shown in column 1 (p for plasmid and BTI for Biosearch Technlogies Inc.) The names of the original vectors are in column 2. pSecTag2A is a shuttle plasmid for maintenance and cloning in *E. coli* and for Cytomegalovirus driven expression in animal cells of the inserted gene as an intra- or extracellular protein with possible fusion to myc and His6 tags for immnuorecognition and metal column affinity chromatography. As is known in the art, the pET28 plasmid confers kanamycin resistance in *E. coli* and also provides high level expression in *E. coli* strains harboring the DE3 lysogen (T7 RNA polymerase under lactose control). The inserted gene sequence may be directly fused to N- or C-terminal $His_6$ peptides. A brief description of the proteins encoded by the plasmids are in column 3. Abbreviations are wt: wild type; C70V (Cys 70 Val mutant), IgKappa leader: The azoreductase is preceeded by a signal sequence form immunoglobulin Kappa chain which permits entry into the endoplasmic reticulum and ensuing sectretion out of the cell. C-term myc is a short peptide from the c-myc protein fused to azoredutasae for immunoregognition in the abence of azoredutase specific antibodies. The C-term His6 peptide is fused to azoreductase and allows for immnuorecognition and metal column affinity chromatography. C-term Cys refers to single or multiple added Cysteins between the myc and His tags to enable specific crosslinking to other proteins, nucleic acids or small molecules.

To create the plasmids shown in Table 3, optimized wt and C70V synthetic genes were cloned into the SfiI and ApaI sites of pSecTag2a (Invitrogen) between the Immunoglobulin Kappa chain (IgK) leader and the Myc and $His_6$ tags, to make pBTI3 and -4. One NheI site between the T7 promoter and the IgK start codon and a second engineered 5' of BTI1 was used to remove the IgK leader sequence to create pBTI5 and -6. BTI1 wt and C70V±the IgK leader and inserted into the HindIII (blunt) and NcoI sites of pET28 (Novagen) to constitute pBTI7-10. Plasmid-sequencing made use of flanking sequencing primer sites. The pSecTag2 vector utilizes: T7 promoter and bGH polyA, and the pET28 vector utilizes: T7 promoter and T7 terminator. Large-scale plasmid preparations employ Qiagen reagents and the endotoxin free protocol.

Expression in *E. coli* and Purification

Novagen's Studier-based expression system from pET28 is used in conjunction with the self-lysing strain BL21 (DE3) pLysS. Purification of BTI1-protein variants is according to the manufacturer's recommendations, but also employs titrations of imidazole for optimal elution of His-tagged BTI1, and if need be, inclusion body extraction with urea and subsequent refolding.

In Vivo Expression and Choice of Cell Lines

Initially BTI1 expression is tested in CHO-K1 (Chinese Hamster Ovary epithelial) cells that are easily grown and transfected, but may also be employed in other cell lines such as A549 (Human lung epithelial), CV-1 (African Green Monkey kidney fibroblast), HL-60 (Human promyeloblast), HUV-EC-C (Human Umbilical Vascular Endothelial Cells), MCF7 (Human mammary epithelial), and NIH/3T3 (Mouse embryo fibroblast). These animal cell lines are free of virus and thus classified in biosafety level 1 (BL1). The pSecTag2 CMV promoter efficiency also displays a wide range (from 150 arbitrary units (au) for NIH3T3 to 1429 au for HU-VE-C, where 100 au is set as baseline in J558L [human astrocytoma]) letting the user address post-transcriptional aspects of BTI1 protein accumulation. The cell lines, which have all been previously successfully transfected, are maintained in standard DMEM and RPMI media as recommended by the supplier (American Type Culture Collection (ATCC)), and stocks kept frozen at −180° C. The number of cell lines may be expanded to maximize the versatility of using BTI1 as a reporter gene and include the widely used BL2 cell lines COS, HeLa, and NHEK293.

The IgK leader fused to BTI1 is used to produce BTI1 from pBTI3 (and -4) secreted into the cell culture medium. Some of the advantages to assaying for reporter proteins in the medium include the fact that under these conditions there is no need for cell lysis, there is minimal interference of the reporter protein with the intracellular metabolism, and the reporter protein is protected from intracellular proteases.

BTI1 as an intracellular reporter is tested with pBTI5 (and -6) with the empty pSecTag2a as a negative control for expression, and pSecTag2PSA (C-terminally myc-tagged Prostate Specific Antigen) as a positive control (both included from Invitrogen). As a control for transfection efficiency, the gWiz High-Expression GFP vector (Gene Therapy Systems [GTS]) is co-transfected. The gWiz High-Expression SEAP and gWiz Beta-gal vectors (GTS) serves dual purposes as a positive control for reporter gene expression and as the first of many possible duplexing partners for azoreductase.

Transfection with reagents such as Transfectam or Trans-Fast (Promega) is performed according to the manufacturer's recommendations. In brief, for Transfectam: 5 µg endotoxin-free plasmid DNA in 50 µl 150 mM NaCl is added to 10 µl Transfectam and thoroughly mixed. After 10 min, the mix is added to 50-70% confluent cells in 60 mm dishes in 1.5 ml medium. After another 2 h 4 ml medium is added and the cells incubated over night. The amount of DNA and transfection reagent as well as the incubation times may be varied to determine optimal conditions for expression of azoreductase and other reporter genes. In case of low transfection efficiency and BTI1 expression, Transfectam and TransFast may be replaced by any of many commercially available transfection reagents such as CellPhect (Amersham) or GeneJuice (Novagen).

Transfection efficiency (%) is assessed by counting greenly fluorescing cells in a microscope such as Nikon Eclipse E 800. Viable cell count is similarly done after staining with Trypan Blue.

Cells expressing pBTI5, or pSecTag2a, and gWiz Beta-Gal are lyzed in 200 mM Tris, 0.1% Triton X-100, pH 7.0 for 10 on ice. Cell debris is removed by centrifugation at 10,000×g in a microfuge and the supernatant used to assay β-gal (below) and azoreductase activity as described in for example, Example 5 (above). NADPH is first added to the reaction mixture at a concentration of 100 µM, together with the substrate at 6 µM. Activity of BTI1 and SEAP are measured in medium from cells expressing pBTI3, or pSecTag2PSA, and gWiz SEAP. When necessary, lysates and media are be diluted in appropriate buffers, such as 200 mM Tris-Cl, pH 7.0, to achieve quantifiable signals. Experiments are performed in triplicate at minimum.

Both β-gal and SEAP activity are quantified with 4-methylumbelliferone derivatized with β-D-galactopyranoside (β-gal) and phosphate (SEAP) from Bio-Tek and Invitrogen. Emitted light at 460 nm is measured after excitation at 365 nm in a CytoFluor II or a Spectramax Gemini and analyzed with SoftMaxPro. Alternative fluorescent substrates that release fluorescein (Invitrogen) and chemiluminescent substrates from ABI for β-gal (GalactoLight) and SEAP (Phospha-Light), may be used in place of 4-MUG. Potential backup for β-gal and 4-MUG is β-GUS and ImaGreene (Invitrogen).

Activity of BTI1 expressed in bacteria and mammalian cells may be compared. First serially diluted bacterial BTI1 is added to cell lysates or cell culture medium for a side by side comparison. Next, BTI1 from CHO-cells is purified by Ni-affinity column and compared to BTI1 purified from overexpressing *E. Coli*. Current data suggests that the established fluorophores for cell studies FAM and TAM perform well in combination with BHQ-1 and -2. However, any suitable substrate is useful in the practice of the invention.

Measured azoreductase activity is also correlated with the amount of full length BTI1 present in the cell medium or cell lysate, taking advantage of the C-terminal Myc-epitope and Ni-column purified BTI1 from bacteria expressing pBTI7-10 (FIG. 13) in western analysis. Azoreductase is expressed and remains stable at levels sufficient for detection by the calorimetric Western Breeze kit (Invitrogen), or the Amersham ECL Plus method and Alpha Innotech's ChemiImager. Alternatively the pro-Q oligoHis stain is used (Invitrogen), to circumvent immunodetection. Western analysis also gives an indication of proper processing of the IgK leader in cells expressing pBTI3 (and -4) (FIG. 13) and using myc-tagged PSA as a positive control for processing. Anomalies in protein size, indicating possible post-translational modifications, may be investigated with the glycoprotein stain pro-Q300 (Molecular Probes) and by subjecting affinity-purified BTI1 to suitable combinations of Mass Spectrometry (LC-MS, MS-MS, MALDI-TOF etc.), before and after treatment with glycosylases.

Taken together, the outlined experiments directly test azoreductase as a reporter gene in one or more mammalian cell lines. They also benchmark the strength and reproducibility of the azoreductase dependent fluorescent signal against other reporter systems. It is possible to measure azoreductase-dependent signals concurrent with at least one other reporter. Differential subcellular localization of BTI1 may be achieved by fusing known organellar targeting sequences to its N- and or C-termini.

Example 7
Enzymatics of Azoreduction In Vitro and Development of Pro-Fluorescent Substrates to Generate Easily Quantifiable Long-Lived Signals The following example illustrates development of a versatile BTI1 reporter system comprising multiple enzyme variants and suitable substrates. Experiments are outlined here which (I) streamline BTI1-production and (II) evaluate azoreduction of Black Hole Quenchers in new Quencher Fluorophore (Q-F) paired substrates.

(I) Expression and Purification of BTI1 in Bacteria

BTI1 is overexpressed in *E. coli* BL21(DE3)pLysS from pBTI7, -8, -9, and -10, by induction with IPTG. BTI1 protein extracts are made by freeze-thaw induced cell lysis in Tris buffer and centrifugation at 10,000×g to separate soluble from insoluble material. Overexpression and partition of BTI1-variants into either fraction will be determined by SDS-PAGE stained with GelCode (Pierce). Soluble protein is then passed through a 2 µm filter to remove particles and aggregates. His-tagged protein is allowed to bind Ni-NTA resin, washed with 200 mM imidazole in Tris buffer and eluted with 500 mM imidazole. Azoreductase-containing fractions is identified by SDS-PAGE and pooled. Pure BTI1-variants are concentrated and the buffer exchange by three rounds of centrifugation through Centricon-30 (Millipore). Protein concentration is determined with the Bradford assay (Pierce). The IgK leader can cause protein aggregation. If so, IgK-linked BTI1 is solubilized in the initial cell lysate with increasing concentrations of urea. High purity of the leader-equipped BTI1 from bacteria is not essential as it's main use will as a size marker for eukaryotic BTI1-expression from pBTI5 and -6.

Initial enzymology makes use of BTI1 (wt) expressed from pBTI9 and BHQ2-TAM. This substrate was chosen because it is easily made, compatible quencher fluorophore spectral overlap, much lower pH dependent fluorescence than FAM, and has a high extinction coefficient.

The kinetics of BTI1-mediated reduction of the TAM-BHQ2 pair starting from the assay described in below, and/or as in Example 5. The reaction mixture comprises the enzyme in 20 mM Tris buffer at pH 7.0, with 250 µM NADPH and 20 µM substrate. The rate of the reaction is measured at various substrate and NADPH concentrations to determine the Km(substrate), Km(NADPH), Vmax, and optimal conditions for the assay as is known in the art. The expected products of enzymatic vs. chemical azoreduction by dithionate will be verified by LC-MS on small molecules from the reaction.

(II) Fluorophore Quencher Substrates
(a) Selection

T poly-aromatic azo Black Hole Quencher (BHQ) dyes, are among the most efficient quencher dyes available. Further, fluorescent Cal Fluor and Quasar dyes of the xanthene and cyanine classes, permit fluorophore emission wavelengths to be selected up to 700 nm. The structure of an exemplary BHQ-fluorophore pair is shown below.

for BTI1 in terms of initial velocity, Km(substrate) and signal to noise ratio. Results from enzymatic azoreduction also give information on the fluorophore contribution of Q-F pairs as substrates for BTI1. The Table below shows a spectrum of proposed quencher-fluorophore paired substrates for BTI1

TABLE 4

| A spectrum of proposed quencher-fluorophore paired substrates for BTI1 | | | | | |
|---|---|---|---|---|---|
| BHQ ($\lambda_{max}$ nm) | BHQ 0 (495) | BHQ 10 (510) | BHQ 1 (534) | BHQ 2 (579) | BHQ 3 (625) |
| Fluorophore | Alexa 350 EDANS | FAM, CAL Gold 540 JOE | Alexa 488 FAM, Alexa 430 CAL Gold 540 JOE CAL Orange 560 | Quasar 570 TAM CAL Red 590 CAL Red 610 CAL Red 635 Pulsar 650 Quasar 670 | Pulsar 650 Quasar 670 |

PRO-FLUORESCENT BHQ-FLUOROPHORE PAIRS

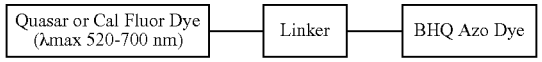

The linker may be inert or it may possess chemical functionality that can act as a substrate for enzymes other than azoreductase such as, esterases, endo-peptidases and endo-glycosylases. Thus the basic fluorophore-linker-quencher construct is general and can function to monitor a number of processes. Appropriate choice of linker and dye (emission wavelength) can permit simultaneous detection and monitoring of multiple enzyme activities. Diazotization of the amino group followed by coupling to a second aromatic group of molecules such as those in FIG. 14, will generate a non-fluorescent azo dye. Such dyes can in turn be coupled to a fluorophore to create novel quencher fluorophore pairs that release two independent fluorescent signals upon azoreduction. An example would be BHQ3-Quasar 670, with excitation and emission wavelengths distinct enough to allow detection of each product by excitation at 557 and 649 nm respectively, and recording of the emitted light at 621 and 670 nm respectively. BTI1 efficiently releases fluorescent signals from multiple quencher fluorophore pairs.

The number quencher-fluorophore (Q-F) pairs is expanded, and Q-F pairs are selected from among suitable BHQ and non-azo-fluorophore combinations, taking into consideration excitation and emission spectra (450-670 nm), fluorescence intensity, pH-sensitivity and hydrophobicity. Other commercially available fluorophores may substitute for fluorophores that display undesirable properties when assayed.

(b) Synthesis

Q-F substrates are easily made from available reagents and purified by established methods. For example: The 6-carboxyfluorescein (FAM)-BHQ2 pair is made by coupling the FAM phosphoramidite to BHQ2 glycolate CPG by standard solid phase synthesis on a Biosearch 8700 DNA synthesizer, followed by HPLC purification.

(c) Stability and Substrate Efficiency

Q-F pairs are evaluated based on dark quenching, chemical azoreduction and enzymatic azoreduction. Substrates are ranked according to initial quenching and substrate efficiency It is also desirable to assess the survival of efficient Q-F pairs in culture media and cell lysates. The increase in fluorescence over time in media and in lysates, with or without BTI1, are monitored and identify non-specific reactions and disqualify sensitive Q-F pairs. In this process, substrates are also eliminated whose fluorescence is quenched by media and cell lysate components, even after azoreduction of the BHQ-moiety.

Example 8
In Vitro Applications of BTI1

The following example illustrates some exemplary in vitro applications for BTI1. The applicability of BTI1 in assays such as immunodetection systems will be assessed with enzyme non-covalently bound (I) to secondary antibodies and streptavidin in combination with pro-fluorescent substrates. Alternatively, (II) a crosslinkable BTI1 variant is made, crosslinked (III) to secondary antibodies and streptavidin and tested in combination with pro-fluorescent substrates.

Direct measures to determine the utility of azoreductase include: a) measurement of activity that is retained when bound to other proteins, such as antibodies; b) Enzymatic activity comparable to wild type BTI1 of a point mutated azoreductase (Cys70Val); and c) the retention of activity in free and crosslinked Cys70Val azoreductase engineered with a single C-terminal cysteine.

(I) Activity of Azoreductase Bound to Other Proteins

Two conceptually simple experiments are used to test the activity of BTI1 when bound to antibodies:

(1) BTI1 from pBTI9 are assayed as described below, but with increasing concentrations of mouse monoclonal anti-myc antibody (Invitrogen) that recognizes the C-terminal extension of azoreductase or as a control, in the presence of mouse anti-FLAG antibody that does not bind BTI1.

(2) Reverse immunoblotting tests BTI1-activity when bound to nitrocellulose filter. Goat anti-mouse-myc antibodies (Amersham) are spotted in a 5-fold dilution series on to Hybond ECL (Amersham) NC filter. The remaining protein binding sites on the filter are blocked by 5% dried milk in TBS-T (Tween in Tris buffered saline). Next, the filter is incubated with mouse myc-antibody that binds the spotted goat antibodies. Excess anti-myc antibody is removed with successive washes of TBS-T. Myc-tagged BTI1 (wt and C76V separately) are added to allow the exposed myc-tag to bind to the second antibody in the sandwich. Finally, activity is tested by the addition of TAM-BHQ2 substrate and cofactor in Tris buffer. Signal is monitored by excitation at 540 nm and emission at 600 nm as it develops in a ChemiImager (Alpha Innotech). As controls, either antibody will be omitted to verify that the generated signal depends on the specific binding of BTI1 to the antibody-sandwich, and BTI1 will be omitted to verify that the signal arises from enzymatic azoreduction.

(II) Crosslinkable BTI1

BTI1 C76V, where the single cysteine in the hydrophobic core has been replaced with valine, C76A, C76I, and C76L mutants and cysteine-free azoreductases are tested for activity. A single cysteine close to the C-terminus of BTI1 to be engineered for chemical crosslinking. Annealed phosphorylated dsDNA-oligonucleotides encoding the of $H_3N$-ACA-COOH peptide will be inserted between the SalI and EagI restriction sites in pBTI10 (FIG. 13) to make pBTI11. Correct insertion is verified by restriction digestion and bi-directional sequencing. The single cysteine between the myc and His6-tags provides an exposed handle for crosslinking. More than one cysteine can be inserted. Care is taken to avoid undesirable intra- and inter-molecular cystines. Engineering of a single exposed lysine in azoreductase is not feasible because of the multiple lysines required for binding of NADPH. Protein is expressed in and purified from *E. coli* and tested for activity as above in Example 5.

(III) BTI1 as In Vitro Reporter

BTI1 is employed in multiple assays to detect protein, nucleic acids, complex sugars or small molecules.

For example, streptavidin is a tetrameric protein that binds biotin with very high affinity. This interaction is widely employed in diverse recognition and detection applications. Many conjugates of streptavidin and antibodies with enzymatic reporters such as HRP and APs are commercially available, as well as with small molecules such as FAM and with protein (phycoerythrin) fluorophores. Because protocols for streptavidin-conjugates are well established, conjugates between BTI1 and streptavidin, and antibodies are generated.

Several cross-linking reagents are commercially available to achieve this goal. The Controlled Protein-Protein Cross-Linking Kit from Pierce offers flexibility and minimal dimer formation. The kit uses Sulfo-SMCC to link a thiol group in one protein with an amino group of another. Reaction first with the epsilon amine of a free lysine on streptavidin produces a maleimide-activated protein ready for coupling with the free thiol on BTI1 (from pBTI11). Enzymatic activity of the resulting conjugate will first be with the assay described in for example, Example 5.

After confirming that conjugation has not altered azoreductase activity, BTI1-streptavidin is tested as a replacement for a labeled streptavidin in a commercially available kit for western and ELISA. For western analysis a FLAG-tagged soluble protein, such as a translation factor, is made in bacteria and extracts separated by SDS-PAGE. Proteins are transferred by electro-blotting to a Hybond NC filter. The filter is blocked with dry milk, and the translation factor is detected by a sandwich of a primary anti-FLAG antibody, a secondary biotinylated antibody and finally streptavidin-crosslinked BTI1 to generate a fluorescent signal.

BTI1 is tested for use in ELISA by replacing HRP-streptavidin in the p53 ELISA kit from Zymed with BTI1-stretpavidin. This and similar kits are sold with positive controls for the analyte, allowing straightforward testing of the conjugate in this format.

The present invention provides novel assays based on inducible fluorescence, and probes that are of use in these assays. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

---

What is claimed is:

1. A mixture comprising:
   (a) a probe comprising a fluorophore and a quencher joined by a linker, wherein said quencher is a substrate for an azoreductase, wherein said quencher and said linker have the structure:

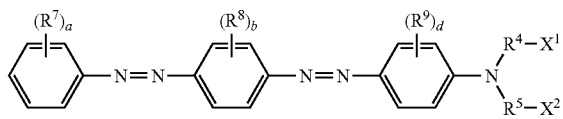

wherein
   R$^4$ and R$^5$ are members independently selected from substituted or unsubstituted alkyl and substituted or unsubstituted heteroalkyl;
   R$^7$, R$^8$ and R$^9$ are members independently selected from H, —NR$^{10}$R$^{11}$, substituted or unsubstituted aryl, nitro, substituted or unsubstituted C$_1$-C$_6$ alkyl, substituted or unsubstituted C$_1$-C$_6$ heteroalkyl, and OH
   wherein
   R$^{10}$ and R$^{11}$ are independently selected from H, substituted or unsubstituted alkyl and substituted or unsubstituted heteroalkyl;
   a is an integer from 0 to 4;
   b is an integer from 0 to 4; and
   c is an integer from 0 to 4; and
   X$^1$ and X$^2$ are members independently selected from —CH$_3$, and a bond to said fluorophore, and at least one member selected from X$^1$ and X$^2$ is said bond to said fluorophore; and
   (b) a cell expressing said azoreductase, said cell comprising a vector comprising a nucleic acid coding said azoreductase operably linked to a promoter.

2. A mixture comprising:
   (a) a probe comprising a fluorophore and quencher joined by a linker, wherein said quencher is a substrate for an azoreductase, wherein said quencher and said linker have the structure:

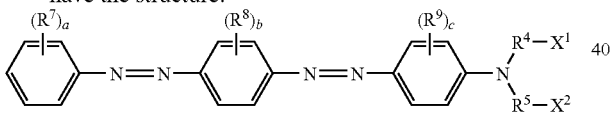

wherein
   R$^4$ and R$^5$ are members independently selected from substituted or unsubstituted alkyl and substituted or unsubstituted heteroalkyl;
   R$^7$, R$^8$ and R$^9$ are members independently selected from H, —NR$^{10}$R$^{11}$, substituted or unsubstituted aryl, nitro, substituted or unsubstituted C$_1$-C$_6$ alkyl, substituted or unsubstituted C$_1$-C$_6$ heteroalkyl, and OH
   wherein
   R$^{10}$ and R$^{11}$ are independently selected from H, substituted or unsubstituted alkyl and substituted or unsubstituted heteroalkyl;
   a is an integer from 0 to 4;
   b is an integer from 0 to 4; and
   c is an integer from 0 to 4; and
   X$^1$ and X$^2$ are members independently selected from —CH$_3$, and a bond to said fluorophore, and at least one member selected from X$^1$ and X$^2$ is said bond to said fluorophore; and
   (b) a cell expressing said azoreductase, said cell comprising a vector comprising a nucleic acid coding said azoreductase operably linked to a promoter, wherein said nucleic acid has a sequence according to SEQ ID NO: 1.

3. The mixture according to claim 1, wherein said azoreductase is conjugated to a target species.

4. The mixture according to claim 1, wherein said azoreductase is conjugated to a binding partner for a target species.

5. The mixture according to claim 1, wherein said probe is conjugated to a target species.

6. The mixture according to claim 1, wherein said probe is conjugated to a binding partner for a target species.

7. The mixture according to claim 1, wherein said quencher has substantially no native fluorescence.

8. The mixture according to claim 1, wherein said quencher has an absorbance maximum of from about 400 nm to about 1000 nm.

9. The mixture according to claim 8, wherein said quencher has an absorbance maximum of from about 500 nm to about 760 nm.

10. The mixture according to claim 1, wherein said azoreductase is a recombinant azoreductase.

11. The mixture according to claim 1, wherein said reductase is a fusion protein comprising a first peptide domain having azoreductase activity and a second peptide domain.

12. The mixture according to claim 11, wherein said second peptide domain is an antibody or a fragment thereof maintaining antigen binding ability.

13. A mixture comprising:
   (a) a probe comprising a fluorophore and quencher joined by a linker, wherein said quencher is a substrate for an azoreductase, wherein said quencher and said linker having a structure that is a member selected from:

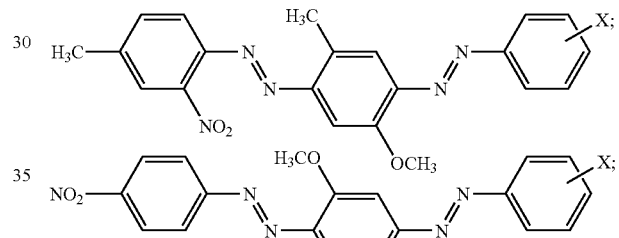

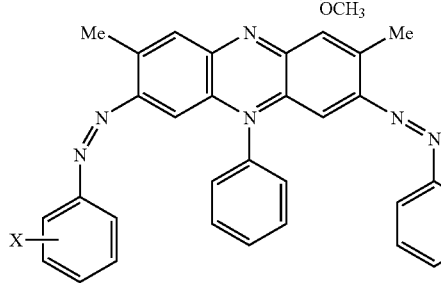

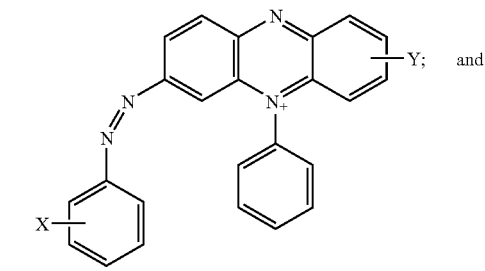

and

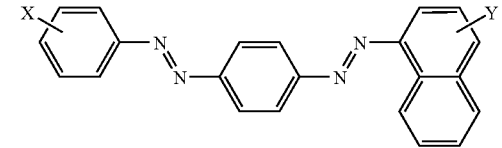

wherein,
in the absence of Y, X is a bond to said fluorophore, or a linker bound to said fluorophore,
in the presence of Y, X and Y are members independently selected from H, a bond to said fluorophore, and a linker bound to said fluorophore, with the proviso that at least one of X and Y is said bond to fluorophore or said linker bound to fluorophore H; and (b) a cell expressing said azoreductase, said cell comprising a vector comprising a nucleic acid coding said azoreductase operably linked to a promoter.

14. The mixture according to claim 1, wherein said probe is a member selected from:

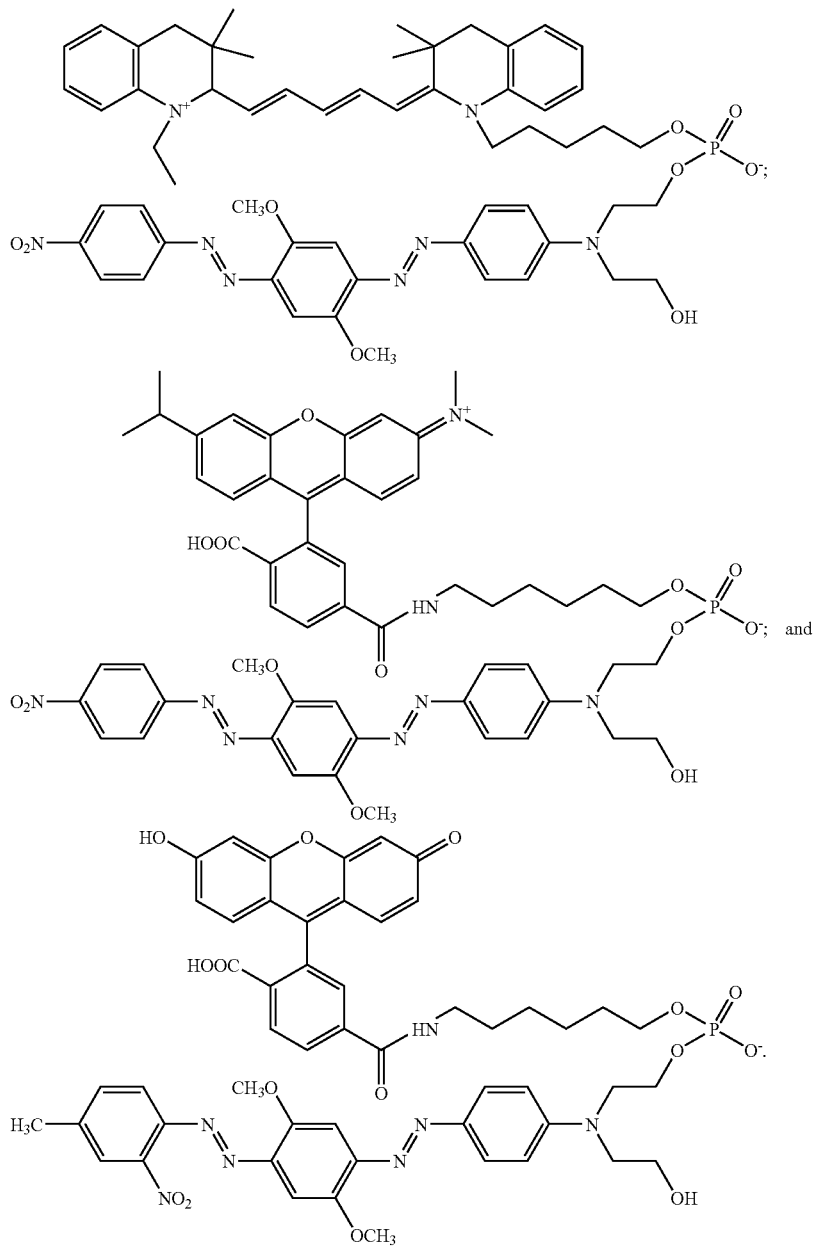

* * * * *

SEQUENCE LISTING

```
<160> NUMBER OF SEQ ID NOS: 9

<210> SEQ ID NO 1
<211> LENGTH: 537
<212> TYPE: DNA
<213> ORGANISM: Bacillus sp.

<400> SEQUENCE: 1
atgaaactag tcgttattaa cggtacacca agaaaattag gtagaactcg cgttgtggca      60
aaatatattg cagatcaatt tgaaggggaa ttatacgatt tagcaataga ggaattgcct     120
ttatataatg gcgaagaatc gcaacgtgat ttagaggcag taaaaaaatt aaaagcgtta     180
gtgaaagcag cagacggtgt agtactatgt acaccagaat atcataatgc aatgagcgga     240
gcgctgaaaa actcgttaga ttacttaagt agtagtgagt ttatccataa acctgtcgca     300
ttactagctg ttgcggttgc tagaggtgtt tacgcaaatg caatcccaaa acaagtagta     360
gggggcggta aaggaggaat taacgcatta aatagtatgc gaactcttga tggacttcac     420
gtacaagatg gtgaacttgg agaagatgca aaaccattaa ttcatgatgt agttaaagaa     480
ttaaaagcat atatgagcgt atataaagag gtgaaaaaac aactaggagt ggagtga       537

<210> SEQ ID NO 2
<211> LENGTH: 178
<212> TYPE: PRT
```

<213> ORGANISM: Bacillus sp.

<400> SEQUENCE: 2

Met Lys Leu Val Val Ile Asn Gly Thr Pro Arg Lys Leu Gly Arg Thr
1               5                   10                  15

Arg Val Val Ala Lys Tyr Ile Ala Asp Gln Phe Glu Gly Glu Leu Tyr
            20                  25                  30

Asp Leu Ala Ile Glu Glu Leu Pro Leu Tyr Asn Gly Glu Glu Ser Gln
        35                  40                  45

Arg Asp Leu Glu Ala Val Lys Lys Leu Lys Ala Leu Val Lys Ala Ala
    50                  55                  60

Asp Gly Val Val Leu Cys Thr Pro Glu Tyr His Asn Ala Met Ser Gly
65                  70                  75                  80

Ala Leu Lys Asn Ser Leu Asp Tyr Leu Ser Ser Glu Phe Ile His
                85                  90                  95

Lys Pro Val Ala Leu Leu Ala Val Ala Val Arg Gly Val Tyr Ala
            100                 105                 110

Asn Ala Ile Pro Lys Gln Val Val Gly Gly Lys Gly Gly Ile Asn
        115                 120                 125

Ala Leu Asn Ser Met Arg Thr Leu Asp Gly Leu His Val Gln Asp Gly
    130                 135                 140

Glu Leu Gly Glu Asp Ala Lys Pro Leu Ile His Asp Val Val Lys Glu
145                 150                 155                 160

Leu Lys Ala Tyr Met Ser Val Tyr Lys Glu Val Lys Lys Gln Leu Gly
                165                 170                 175

Val Glu

<210> SEQ ID NO 3
<211> LENGTH: 537
<212> TYPE: DNA
<213> ORGANISM: Bacillus sp.

<400> SEQUENCE: 3
atgaaactag tcgttattaa cggtacacca agaaaatttg gtagaactcg cgtggtggca      60
aaatatattg cggatcaatt tgaaggggaa ttatatgatt tagcaattga ggagttacct     120
ttatacaatg gagaagagtc gcaacgtgat ttagaggcag taaaaaaatt aaaaacgtta     180
gtgaaagctg cggatggggt tgtattatgt acaccagaat cataatgc gatgagcggt       240
gcgctgaaaa actctttaga ttacttaagt agtagtgaat ttattcataa accagttgca     300
ttgttagcgg ttgctggtgg cggtaaaggt ggaataaatg cattaaacag catgcacgcg     360
tcgctagcag tgtttatgc aaatgcaatt ccaaaacaag ttgtgcttga tggattacat     420
gtgcaagatg gtgaacttgg ggaagatgca aaaccattaa ttcatgatgt agttaaagaa     480
ttgaaagcat atatgagcgt atataaagag gtgaaaaaac aactaggagt ggagtga       537

<210> SEQ ID NO 4
<211> LENGTH: 174
<212> TYPE: PRT
<213> ORGANISM: Bacillus subtilis

<400> SEQUENCE: 4

Met Asn Met Leu Val Ile Asn Gly Thr Pro Arg Lys His Gly Arg Thr
1               5                   10                  15

Arg Ile Ala Ala Ser Tyr Ile Ala Ala Leu Tyr His Thr Asp Leu Ile
            20                  25                  30

Asp Leu Ser Glu Phe Val Leu Pro Val Pro Asn Gly Glu Ala Glu Gln

```
                35                  40                  45
Ser Glu Leu Leu Lys Val Gln Glu Leu Lys Gln Arg Val Thr Lys Ala
 50                  55                  60

Asp Ala Ile Val Leu Leu Ser Pro Glu Tyr His Ser Gly Met Ser Gly
 65                  70                  75                  80

Ala Leu Lys Asn Ala Leu Asp Phe Leu Ser Ser Glu Gln Phe Lys Tyr
                 85                  90                  95

Lys Pro Val Ala Leu Leu Ala Val Ala Gly Gly Lys Gly Gly Ile
                100                 105                 110

Asn Ala Leu Asn Asn Met Arg Thr Val Met Arg Gly Val Tyr Ala Asn
                115                 120                 125

Val Ile Pro Lys Gln Leu Val Leu Asp Pro Val His Ile Asp Val Glu
                130                 135                 140

Asn Ala Thr Val Ala Glu Asn Ile Lys Glu Ser Ile Lys Glu Leu Val
145                 150                 155                 160

Glu Glu Leu Ser Met Phe Ala Lys Ala Gly Asn Pro Gly Val
                165                 170

<210> SEQ ID NO 5
<211> LENGTH: 174
<212> TYPE: PRT
<213> ORGANISM: Bacillus subtilis

<400> SEQUENCE: 5

Met Asn Met Leu Val Ile Asn Gly Thr Pro Arg Lys His Gly Arg Thr
 1                   5                  10                  15

Arg Ile Ala Ala Ser Tyr Ile Ser Ala Leu Tyr His Thr Asp Leu Ile
                 20                  25                  30

Asp Leu Ser Glu Phe Ile Leu Pro Ile Pro Asn Gly Glu Ala Glu Gln
                 35                  40                  45

Ser Glu Leu Leu Gln Val Gln Glu Leu Lys Gln Arg Val Thr Lys Ala
 50                  55                  60

Asp Ala Ile Val Leu Ile Ser Pro Glu Tyr His Ser Gly Met Ser Gly
 65                  70                  75                  80

Ala Leu Lys Asn Ala Leu Asp Tyr Leu Ser Ser Glu Gln Phe Lys Tyr
                 85                  90                  95

Lys Pro Val Ala Leu Leu Ala Val Ala Gly Gly Lys Gly Gly Ile
                100                 105                 110

Asn Ala Leu Asn Asn Met Arg Thr Val Met Arg Gly Val Tyr Ala Asn
                115                 120                 125

Val Ile Pro Lys Gln Leu Val Leu Asp Pro Val His Ile Asp Ile Glu
                130                 135                 140

Asn Ala Ala Val Thr Glu Asn Ile Lys Val Ser Ile Lys Glu Leu Val
145                 150                 155                 160

Glu Glu Leu Ser Met Phe Ala Lys Ala Gly Asn Pro Gly Val
                165                 170

<210> SEQ ID NO 6
<211> LENGTH: 178
<212> TYPE: PRT
<213> ORGANISM: Bacillus cereus

<400> SEQUENCE: 6

Met Lys Leu Val Val Ile Asn Gly Thr Pro Arg Lys Phe Gly Arg Thr
 1                   5                  10                  15

Arg Val Val Ala Lys Tyr Ile Ala Asp Gln Phe Glu Gly Glu Leu Tyr
                 20                  25                  30
```

Asp Leu Ala Ile Glu Glu Leu Pro Leu Tyr Asn Gly Glu Ser Gln
         35                  40                  45

Arg Asp Leu Glu Ala Val Lys Lys Leu Lys Thr Leu Val Lys Ala Ala
 50                  55                  60

Asp Gly Val Val Leu Cys Thr Pro Glu Tyr His Asn Ala Met Ser Gly
 65                  70                  75                  80

Ala Leu Lys Asn Ser Leu Asp Tyr Leu Ser Ser Glu Phe Ile His
                 85                  90                  95

Lys Pro Val Ala Leu Leu Ala Val Ala Gly Gly Lys Gly Gly Ile
             100                 105                 110

Asn Ala Leu Asn Ser Met Arg Thr Val Ala Arg Gly Val Tyr Ala Asn
             115                 120                 125

Ala Ile Pro Lys Gln Val Val Leu Asp Gly Leu His Val Gln Asp Gly
         130                 135                 140

Glu Leu Gly Glu Asp Ala Lys Pro Leu Ile His Asp Val Val Lys Glu
145                 150                 155                 160

Leu Lys Ala Tyr Met Ser Val Tyr Lys Glu Val Lys Lys Gln Leu Gly
                 165                 170                 175

Val Glu

<210> SEQ ID NO 7
<211> LENGTH: 178
<212> TYPE: PRT
<213> ORGANISM: Bacillus subtilis

<400> SEQUENCE: 7

Met Lys Leu Val Val Ile Asn Gly Thr Pro Arg Lys Phe Gly Arg Thr
 1               5                  10                  15

Arg Val Val Ala Lys Tyr Ile Ala Asp Gln Phe Glu Gly Glu Leu Tyr
             20                  25                  30

Asp Leu Ala Ile Glu Glu Leu Pro Leu Tyr Asn Gly Glu Ser Gln
         35                  40                  45

Arg Asp Leu Glu Ala Val Lys Lys Leu Lys Thr Leu Val Lys Ala Ala
 50                  55                  60

Asp Gly Val Val Leu Cys Thr Pro Glu Tyr His Asn Ala Met Ser Gly
 65                  70                  75                  80

Ala Leu Lys Asn Ser Leu Asp Tyr Leu Ser Ser Glu Phe Ile His
                 85                  90                  95

Lys Pro Val Ala Leu Leu Ala Val Ala Gly Gly Lys Gly Gly Ile
             100                 105                 110

Asn Ala Leu Asn Ser Met His Ala Ser Leu Ala Gly Val Tyr Ala Asn
             115                 120                 125

Ala Ile Pro Lys Gln Val Val Leu Asp Gly Leu His Val Gln Asp Gly
         130                 135                 140

Glu Leu Gly Glu Asp Ala Lys Pro Leu Ile His Asp Val Val Lys Glu
145                 150                 155                 160

Leu Lys Ala Tyr Met Ser Val Tyr Lys Glu Val Lys Lys Gln Leu Gly
                 165                 170                 175

Val Glu

<210> SEQ ID NO 8
<211> LENGTH: 178
<212> TYPE: PRT
<213> ORGANISM: Bacillus sp.

<400> SEQUENCE: 8

```
Met Lys Leu Val Val Ile Asn Gly Thr Pro Arg Lys Leu Gly Arg Thr
1               5                   10                  15

Arg Val Val Ala Lys Tyr Ile Ala Asp Gln Phe Glu Gly Glu Leu Tyr
            20                  25                  30

Asp Leu Ala Ile Glu Glu Leu Pro Leu Tyr Asn Gly Glu Ser Gln
        35                  40                  45

Arg Asp Leu Glu Ala Val Lys Lys Leu Lys Ala Leu Val Lys Ala Ala
    50                  55                  60

Asp Gly Val Val Leu Cys Thr Pro Glu Tyr His Asn Ala Met Ser Gly
65                  70                  75                  80

Ala Leu Lys Asn Ser Leu Asp Tyr Leu Ser Ser Glu Phe Ile His
            85                  90                  95

Lys Pro Val Ala Leu Leu Ala Val Ala Gly Gly Lys Gly Gly Ile
            100                 105                 110

Asn Ala Leu Asn Ser Met Arg Thr Val Ala Arg Gly Val Tyr Ala Asn
            115                 120                 125

Ala Ile Pro Lys Gln Val Val Leu Asp Gly Leu His Val Gln Asp Gly
    130                 135                 140

Glu Leu Gly Glu Asp Ala Lys Pro Leu Ile His Asp Val Val Lys Glu
145                 150                 155                 160

Leu Lys Ala Tyr Met Ser Val Tyr Lys Glu Val Lys Lys Gln Leu Gly
                165                 170                 175

Val Glu

<210> SEQ ID NO 9
<211> LENGTH: 191
<212> TYPE: PRT
<213> ORGANISM: Saccharomyces cerevisiae

<400> SEQUENCE: 9

Met Lys Val Gly Ile Ile Met Gly Ser Val Arg Ala Lys Arg Val Cys
1               5                   10                  15

Pro Glu Ile Ala Ala Tyr Val Lys Arg Thr Ile Glu Asn Ser Glu Glu
            20                  25                  30

Leu Ile Asp Gln Lys Leu Lys Ile Gln Val Val Asp Leu Gln Gln Ile
        35                  40                  45

Ala Leu Pro Leu Tyr Glu Asp Asp Glu Leu Ile Pro Ala Gln Ile
    50                  55                  60

Lys Ser Val Asp Glu Tyr Ala Asp Ser Lys Thr Arg Ser Trp Ser Arg
65                  70                  75                  80

Ile Val Asn Ala Leu Asp Ile Ile Val Phe Val Thr Pro Gln Tyr Asn
            85                  90                  95

Trp Gly Tyr Pro Ala Ala Leu Lys Asn Ala Ile Asp Arg Leu Tyr His
            100                 105                 110

Glu Trp His Gly Lys Pro Ala Leu Val Val Ser Tyr Gly Gly His Gly
            115                 120                 125

Gly Ser Lys Cys Asn Asp Gln Leu Gln Glu Val Leu His Gly Leu Lys
    130                 135                 140

Met Asn Val Ile Gly Gly Val Ala Val Lys Ile Pro Val Gly Thr Ile
145                 150                 155                 160

Pro Leu Pro Glu Asp Ile Val Pro Gln Leu Ser Val His Asn Glu Glu
                165                 170                 175

Ile Leu Gln Leu Leu Ala Ser Cys Ile Glu Thr Thr Arg Asn Lys
        180                 185                 190
```